US011330983B2

(12) United States Patent
Lychagov et al.

(10) Patent No.: US 11,330,983 B2
(45) Date of Patent: May 17, 2022

(54) ELECTRONIC DEVICE FOR ACQUIRING STATE INFORMATION ON OBJECT, AND CONTROL METHOD THEREFOR

(71) Applicant: SAMSUNG ELECTRONICS CO., LTD., Suwon-si (KR)

(72) Inventors: Vladislav Valerievich Lychagov, Saratov (RU); Mikhail Vyacheslavovich Popov, G. Krasnogorsk (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/970,149

(22) PCT Filed: Mar. 21, 2019

(86) PCT No.: PCT/KR2019/003301
§ 371 (c)(1),
(2) Date: Aug. 14, 2020

(87) PCT Pub. No.: WO2019/190122
PCT Pub. Date: Oct. 3, 2019

(65) Prior Publication Data
US 2020/0397301 A1    Dec. 24, 2020

(30) Foreign Application Priority Data

Mar. 30, 2018   (RU) ............................ RU2018111477
Mar. 18, 2019   (KR) ........................ 10-2019-0030560

(51) Int. Cl.
*G01N 33/02* (2006.01)
*A61B 5/00* (2006.01)
(Continued)

(52) U.S. Cl.
CPC ............ *A61B 5/0075* (2013.01); *A61B 5/443* (2013.01); *G01N 21/314* (2013.01); *G01N 33/02* (2013.01);
(Continued)

(58) Field of Classification Search
CPC .... A61B 5/0075; A61B 5/443; G01N 21/314; G01N 33/493; G01N 2021/3155; G01J 3/45
See application file for complete search history.

(56) References Cited

U.S. PATENT DOCUMENTS 5,541,728 A   7/1996  Dierking
7,428,046 B2  9/2008  Wang et al.
(Continued)

FOREIGN PATENT DOCUMENTS

CN  101371128 A   2/2009
CN  102812346 A   12/2012
(Continued)

OTHER PUBLICATIONS

Patrick D. Barnett, "Miniature Spatial Heterodyne Raman Spectrometer with a Cell Phone Camera Detector", Applied Spectroscopy 2017 (Year: 2017).*
(Continued)

*Primary Examiner* — Maurice C Smith
(74) *Attorney, Agent, or Firm* — Sughrue Mion, PLLC

(57) ABSTRACT

According to an embodiment of the disclosure, there is provided an electronic device including: an optical element that is fixed and is configured to split incident light reflected from an object into two or more incident light beams traveling along two or more light paths; an optical sensor that is spaced a separation distance from the optical element such that the split incident light beams form an interference area on a light receiving surface and is configured to detect (Continued)

the incident light; and at least one processor configured to determine state information about the object based on similarity between a first spectrum acquired from the detected incident light and at least one reference spectrum.

14 Claims, 18 Drawing Sheets

(51) Int. Cl.
    *G01N 21/31*     (2006.01)
    *G01N 33/483*     (2006.01)
    *G01N 33/493*     (2006.01)
    *H04M 1/725*     (2021.01)

(52) U.S. Cl.
    CPC ....... *G01N 33/4833* (2013.01); *G01N 33/493* (2013.01); *G01N 2021/3155* (2013.01); *H04M 1/725* (2013.01)

(56) References Cited

U.S. PATENT DOCUMENTS

| | | |
|---|---|---|
| 7,907,282 B2 | 3/2011 | Coates |
| 8,027,855 B2 | 9/2011 | Freese et al. |
| 8,094,311 B2 | 1/2012 | Uzunbajakava et al. |
| 8,121,671 B2 | 2/2012 | Hull et al. |
| 8,344,334 B2 | 1/2013 | Coker et al. |
| 8,400,637 B2 | 3/2013 | Myrick et al. |
| 8,727,978 B2 | 5/2014 | Tran et al. |
| 8,747,313 B2 | 6/2014 | Tran et al. |
| 8,830,475 B1 | 9/2014 | Wang et al. |
| 8,841,137 B2 | 9/2014 | DeLouise et al. |
| 8,858,607 B1 | 10/2014 | Jones |
| 9,044,150 B2 | 6/2015 | Brumback et al. |
| 9,049,998 B2 | 6/2015 | Brumback et al. |
| 9,279,720 B2 | 3/2016 | Kamimura |
| 9,480,426 B2 | 11/2016 | Rajagopal et al. |
| 9,536,449 B2 | 1/2017 | Connor |
| 9,995,629 B2 | 6/2018 | Schardt |
| 10,088,363 B2 | 10/2018 | Cho et al. |
| 10,253,346 B2 * | 4/2019 | Auner ..................... G01J 3/44 |
| 10,393,579 B2 | 8/2019 | Herrmann et al. |
| 2004/0115726 A1 | 6/2004 | Nagashima et al. |
| 2008/0189066 A1 * | 8/2008 | Miller .................... G01N 21/65 702/82 |
| 2008/0213904 A1 | 9/2008 | Sliwa et al. |
| 2009/0152475 A1 | 6/2009 | Sasaki et al. |
| 2012/0206050 A1 | 8/2012 | Spero |
| 2013/0034873 A1 | 2/2013 | Schweigert |
| 2013/0038933 A1 * | 2/2013 | Wang .................. G02B 27/283 359/485.04 |
| 2014/0320858 A1 | 10/2014 | Goldring et al. |
| 2015/0035440 A1 | 2/2015 | Spero |
| 2015/0268097 A1 | 9/2015 | Ishimaru |
| 2016/0034764 A1 | 2/2016 | Connor |
| 2016/0109295 A1 | 4/2016 | Wang |
| 2016/0112684 A1 | 4/2016 | Connor |
| 2016/0198994 A1 * | 7/2016 | Murphy .................. A61B 5/445 600/477 |
| 2016/0232811 A9 | 8/2016 | Connor |
| 2016/0290863 A1 | 10/2016 | Goldring et al. |
| 2017/0264834 A1 | 9/2017 | Hegyi et al. |
| 2017/0292908 A1 | 10/2017 | Wilk et al. |
| 2018/0045569 A1 | 2/2018 | Nath et al. |
| 2018/0064378 A1 | 3/2018 | Park et al. |
| 2018/0238794 A1 | 8/2018 | Kangas et al. |
| 2019/0113387 A1 | 4/2019 | Lee et al. |
| 2021/0025753 A1 | 1/2021 | Goldring et al. |
| 2021/0302232 A1 | 9/2021 | Goldring et al. |

FOREIGN PATENT DOCUMENTS

| | | |
|---|---|---|
| CN | 103281459 A | 9/2013 |
| CN | 103900977 A | 7/2014 |
| CN | 104040309 A | 9/2014 |
| CN | 104062007 A | 9/2014 |
| CN | 104215607 A | 12/2014 |
| CN | 105334166 A | 2/2016 |
| CN | 105527269 A | 4/2016 |
| CN | 105593651 A | 5/2016 |
| CN | 105973466 A | 9/2016 |
| CN | 205593911 U | 9/2016 |
| CN | 205754455 U | 11/2016 |
| CN | 106370642 A | 2/2017 |
| CN | 107076665 A | 8/2017 |
| CN | 107084790 A | 8/2017 |
| DE | 10 2015 219 672 A1 | 3/2017 |
| EP | 3 056 880 A2 | 8/2016 |
| KR | 10-1392311 B1 | 5/2014 |
| KR | 10-2016-0106378 A | 9/2016 |
| KR | 10-2017-0106251 A | 9/2017 |
| KR | 10-2017-0143351 A | 12/2017 |
| KR | 10-2018-0027006 A | 3/2018 |
| RU | 2 184 950 C1 | 7/2002 |
| WO | 2006/127840 A3 | 11/2006 |
| WO | 2011/093794 A1 | 8/2011 |
| WO | 2016/039690 A1 | 3/2016 |
| WO | 2016/180551 A1 | 11/2016 |
| WO | 2017/149543 A1 | 9/2017 |

OTHER PUBLICATIONS

Communication dated Dec. 31, 2020 by the State Intellectual Property Office of P.R. China in counterpart Chinese Patent Application No. 201980021100.3.
Communication dated Feb. 18, 2021 by the European Patent Office in counterpart European patent Application No. 19774417.0.
Communication dated Jun. 24, 2019 issued by the International Searching Authority in counterpart Application No. PCT/KR2019/003301 (PCT/ISA/220, PCT/ISA/210, and PCT/ISA/237).
Communication dated Jan. 16, 2019 issued by the Russian Intellectual Property Office in counterpart Russian Application No. 2018111477.
Communication dated May 24, 2021 issued by the Intellectual Property India Patent Office in application No. 202037036409.
Communication dated Aug. 25, 2021, issued by the State Intellectual Property Office of P.R. China in counterpart Chinese Application No. 201980021100.3.
Communication dated Nov. 19, 2021 issued by the State Intellectual Property Office of P.R. China in counterpart Chinese application No. 201980021100.3.

* cited by examiner

FIG. 11
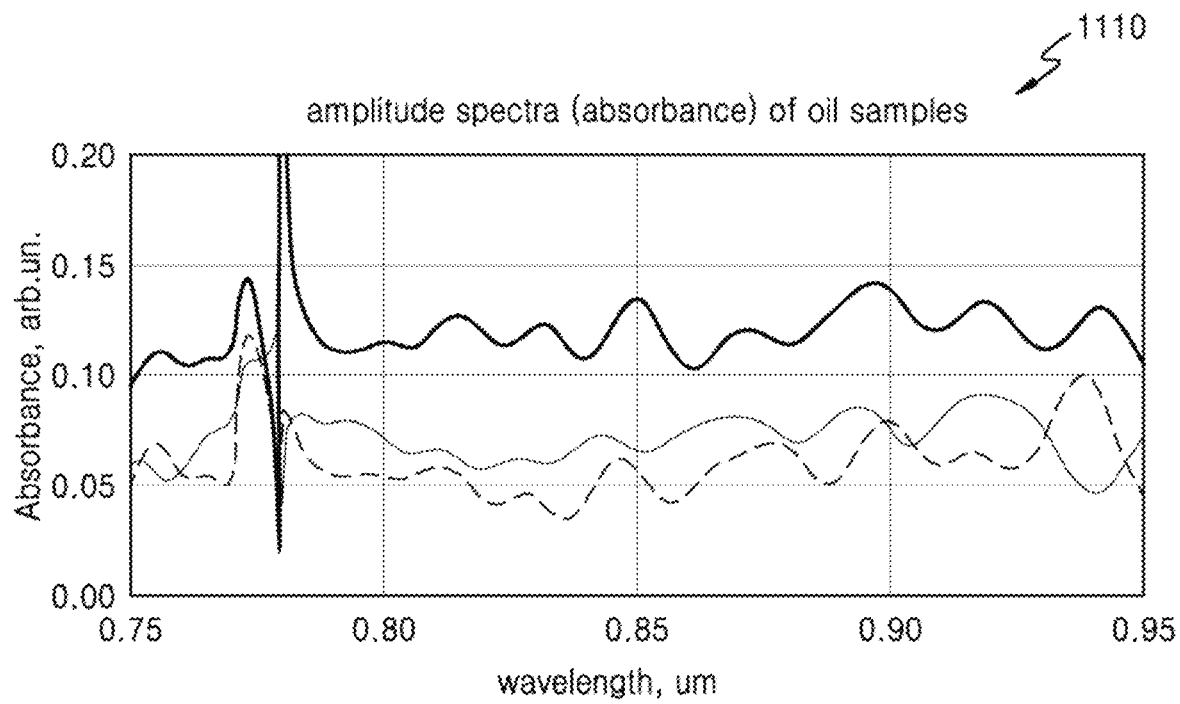
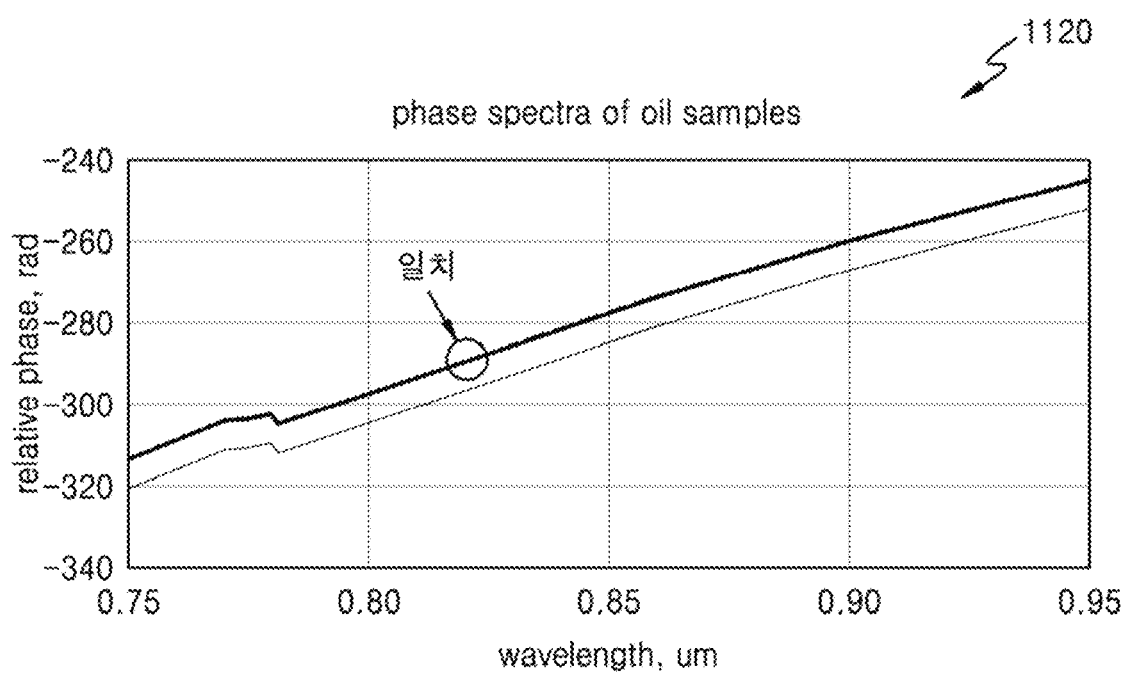

ELECTRONIC DEVICE FOR ACQUIRING STATE INFORMATION ON OBJECT, AND CONTROL METHOD THEREFOR

CROSS-REFERENCE TO RELATED APPLICATIONS

This application is a National Phase Entry of PCT International Application No. PCT/KR2019/003301, filed on Mar. 21, 2019, which claims priority to Russian Patent Application No. 2018111477, filed on Mar. 30, 2018, and Korean Application No. 10-2019-0030560, filed on Mar. 18, 2019.

TECHNICAL FIELD

Embodiments of the disclosure relate to an electronic device, an electronic device control method, and a computer program product for performing the electronic device control method. The embodiments of the disclosure relate to the field of measurement engineering. Also, the embodiments of the disclosure relate to a small device that may be applicable to a wearable electronic device, a mobile device, or other types of electronic devices. The electronic device and the control method thereof according to the embodiments of the disclosure may be applied to various fields for analyzing objects.

BACKGROUND ART

Lately, electronic devices including optical elements are widely used. The electronic devices may include optical systems such as spectrometers.

One type of such spectrometers is disclosed in WO 2016/180551. In WO 2016/180551, a static Fourier transform spectrometer (hereinafter, referred to as a first publicly known spectrometer) including a beam splitter, a mirror apparatus, and a converging optical unit is disclosed. The beam splitter divides an input light beam into a first arm and a second arm, wherein the first arm is reflected by the beam splitter and the second arm passes through the beam splitter. The first arm extends to the converging optical unit without deflection after being reflected by the mirror apparatus. The second arm extends to the converging optical unit without deflection after passing through the beam splitter. The converging optical unit makes the first arm and the second arm converge together for interference. However, the first publicly known spectrometer is incompatible with smart devices, such as smart phones, smart watches, etc., and has a complicated design. These problems limit the fields of use of the spectrometer. Also, the first publicly known spectrometer is incompatible with low-interference light (that is, white light), and requires time, cost, and precise alignment.

U.S. Pat. No. 5,541,728 discloses a stationary Fourier transform spectrometer (hereinafter, referred to as a second publicly known spectrometer) including a beam splitter, an interferometer including a significantly firm assembly of two right angle prisms and a preselected pentaprism, each having an aperture size, a radiation source, a Fourier transform lens, and an optical detector. The second publicly known spectrometer includes expensive optical elements, has a complicated design, and also has difficulties in alignment. Furthermore, the second publicly known spectrometer is incompatible with mobile devices.

The above-described incompatibility problem of mobile devices has been overcome by U.S. Patent No. 2016/0290863, which discloses a compact spectrometer system (hereinafter, referred to as a third publicly known spectrometer) that is suitable for use in mobile devices such as cellphones. In preferred embodiments, the third publicly known spectrometer includes a filter, at least one Fourier transform focusing element, a micro-lens array, and a detector. However, the third publicly known spectrometer does not use an arbitrary dispersion element. U.S. Patent No. 2016/0290863 discloses a method of using the third publicly known spectrometer as a final user device for determining the quality of food on the spot through comparison with updatable database that all users of the device can access. However, the third publicly known spectrometer has a complicated design because it uses an optical filter instead of a plurality of Light Emitting Diodes (LEDs). Also, the third publicly known spectrometer has low spectral resolution due to its similarity to a Light Emitting Diode-Photodiodes (LED-PD) system. Also, the third publicly known spectrometer is used only for food analysis, and has a limited field of use.

Accordingly, the spectrometers of the cited patent documents have complicated designs and difficulties in being sufficiently miniaturized. Therefore, there are difficulties in using the spectrometers in mobile devices. Also, the spectrometers of the cited patent documents have difficulties due to low spectrum resolution that is unsuitable for purposes other than food analysis.

DESCRIPTION OF EMBODIMENTS

Technical Problem

Embodiments of the disclosure are to obtain state information about an object from incident light reflected from the object in an electronic device.

Also, the embodiments of the disclosure are to provide an electronic device that does not require precise alignment of an optical element and a collimator, and a control method of the electronic device.

Also, the embodiments of the disclosure are to apply an optical system including an optical element, a collimator, an optical sensor, etc. to a small electronic device, such as a mobile device, a wearable electronic device, etc., and acquire state information of an object from incident light reflected from the object in the small electronic device.

Also, the embodiments of the disclosure are to detect a wide range of wavelengths by using a plurality of sensors having different wavelength ranges, without adjusting the sensors.

Solution to Problem

An electronic device according to an embodiment of the disclosure includes: an optical element that is fixed and is configured to split incident light thereon reflected from an object into two or more incident light beams traveling along two or more light paths; an optical sensor that is spaced a separation distance from the optical element such that the split incident light beams form an interference area on a light receiving surface and is configured to detect the incident light; and at least one processor configured to determine state information about the object based on similarity between a first spectrum acquired from the detected incident light and at least one reference spectrum.

The electronic device according to an embodiment of the disclosure may further include a collimator that is fixed and is configured to collimate the incident light reflected from the object.

The optical element according to an embodiment of the disclosure may include an axicon that may include two or more faces respectively corresponding to the two or more light paths.

The optical element according to an embodiment of the disclosure may include a plurality of prisms respectively corresponding to the two or more light paths.

The optical sensor according to an embodiment of the disclosure may include a plurality of sub sensors having different wavelength ranges, and the plurality of sub sensors may include at least one or a combination of a first sensor having a wavelength range of 300 nm to 500 nm, a second sensor having a wavelength range of 400 nm to 750 nm, or a third sensor having a wavelength range of 750 nm to 1000 nm.

The processor according to an embodiment of the disclosure may be configured to perform Fourier transform on the incident light to acquire amplitude information and phase information, and determine the similarity between the first spectrum and the at least one reference spectrum based on the amplitude information and the phase information.

The amplitude information and the phase information acquired by performing the Fourier transform, according to an embodiment of the disclosure, may respectively correspond to a real part and an imaginary part.

The processor according to an embodiment of the disclosure may be configured to acquire type information about the object corresponding to the first spectrum, and compare the first spectrum to the at least one reference spectrum corresponding with the type information to determine the state information.

The electronic device according to an embodiment of the disclosure may further include a communicator, wherein the processor may be further configured to obtain the at least one reference spectrum from an external device through the communicator.

The processor according to an embodiment of the disclosure may be configured to determine state information related to health based on a change of portions of spectrum intensities of different two wavelengths.

The processor according to an embodiment of the disclosure may be configured to determine state information related to skin based on a spectrum change of a hydration level upon dehydration and a spectrum change of a hydration level upon rehydration.

The object according to an embodiment of the disclosure may include a first object corresponding to urine and a second object including a mixture of urine and a first compound, and the processor may be configured to determine information related to a disease based on a first spectrum of the first object and a second spectrum of the second object.

The state information according to an embodiment of the disclosure may include at least one of whether a product is a genuine product or a fake product, freshness of food, ripeness, or a degree of cooking.

A control method of an electronic device including an optical element and an optical sensor, according to an embodiment of the disclosure, includes: splitting incident light reflected from an object into two or more incident light beams traveling along two or more light paths in the optical element; detecting the incident light on the optical sensor; and determining state information about the object based on similarity between a first spectrum acquired from the detected incident light and at least one reference spectrum, wherein the optical sensor is spaced a separation distance from the optical element such that the split incident light beams form an interference area on a light receiving surface.

A computer program product includes a recording medium storing program commands, which, when executed by a processor according to an embodiment of the disclosure, cause the processor to perform a method of determining state information about an object, the method of determining the state information about the object including: splitting incident light reflected from an object into two or more incident light beams traveling along two or more light paths in the optical element; detecting the incident light on the optical sensor; and determining state information about the object based on similarity between a first spectrum acquired from the detected incident light and at least one reference spectrum, wherein the optical sensor is spaced a separation distance from the optical element such that the split incident light beams form an interference area on a light receiving surface.

Advantageous Effects of Disclosure

According to embodiments of the disclosure, an electronic device may obtain state information about an object from incident light reflected from the object.

Also, according to the embodiments of the disclosure, an electronic device that does not require precise alignment of an optical element and a collimator, and a method of controlling the electronic device may be provided.

Also, according to the embodiments of the disclosure, by applying an optical system including an optical element, a collimator, an optical sensor, etc. to a small electronic device, such as a mobile device, a wearable electronic device, etc., the small electronic device may obtain state information about an object from incident light reflected from the object.

According to the embodiments of the disclosure, a wide range of wavelengths may be detected by using a plurality of sensors having different wavelength ranges, without adjusting the sensors.

Other features and advantages of the disclosure will be apparent from the following detailed descriptions and the accompanying drawings.

BRIEF DESCRIPTION OF DRAWINGS

FIG. 11 shows an example of determining state information about an object in an electronic device according to an embodiment of the disclosure.

BEST MODE

Figure 1:
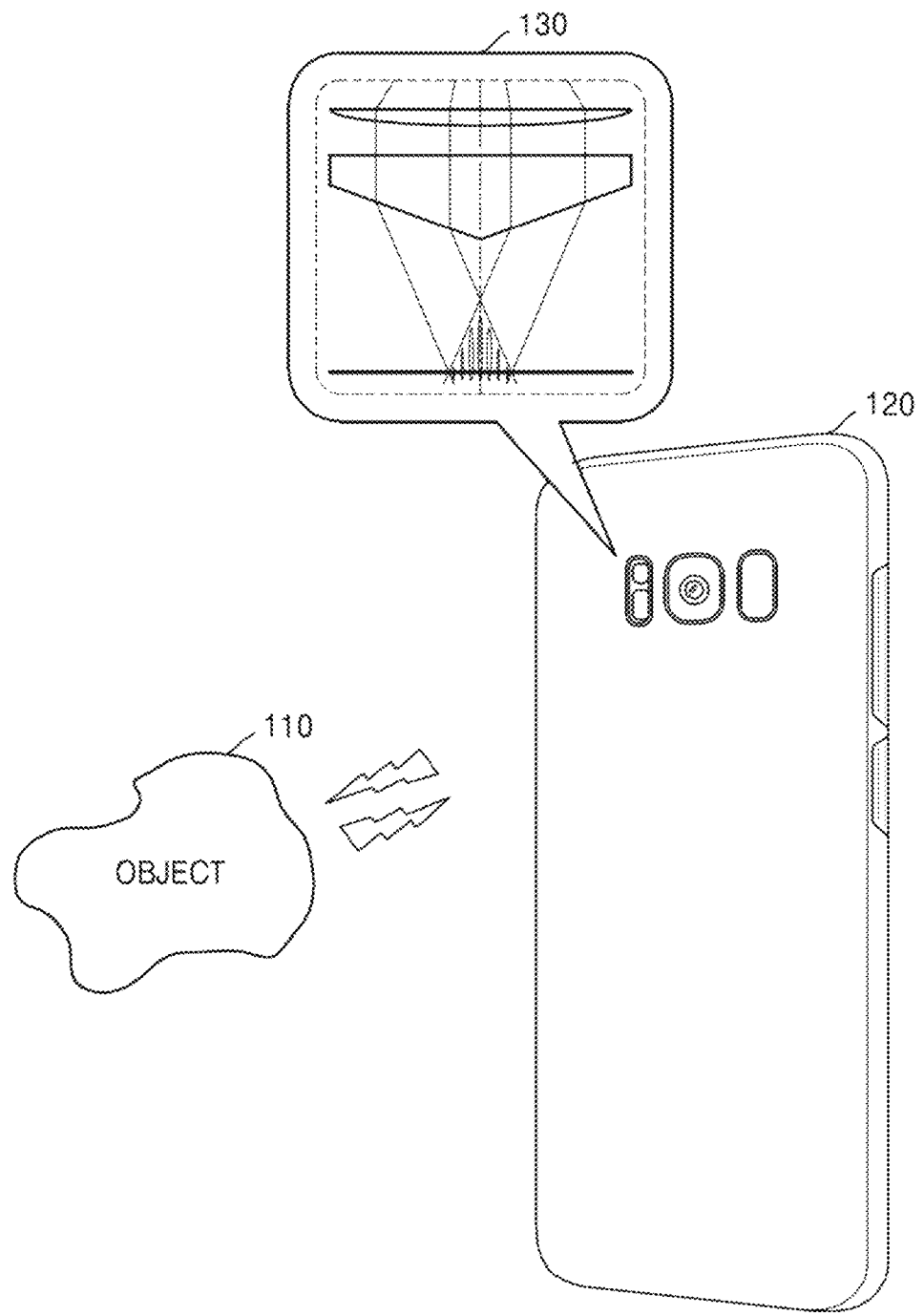
FIG. 1 is a schematic view showing obtaining state information about an object by using an electronic device according to an embodiment of the disclosure.

Hereinafter, various embodiments of the disclosure will be described in detail with reference to the accompanying drawings. However, the disclosure may be implemented in different forms, and is not limited to arbitrary specific structures or functions given in the following description. The embodiments are provided to describe the disclosure in detail and complete the disclosure. According to the descriptions of the disclosure, it will be apparent to those of ordinary skill in the art that the scope of the disclosure includes arbitrary embodiments of the disclosure disclosed in the present specification regardless of whether the embodiments are implemented independently or together with another arbitrary embodiment. For example, a method and device disclosed in the present specification may be implemented actually by using an arbitrary embodiment disclosed in the present specification. The arbitrary embodiment of the disclosure may be implemented by using one or more elements suggested in the claims.

Also, in the drawings, parts that are irrelevant to the descriptions may be not shown in order to clearly describe the embodiments of the disclosure. Throughout the specification, similar parts will be assigned similar reference numerals.

In this specification, it will be understood that the case in which a certain portion is "connected" to another portion includes the case in which the portion is "electrically connected" to the other portion with another device in between, as well as the case in which the portion is "directly connected" to the other portion. Also, it will be understood that when a certain portion "includes" a certain component, the portion does not exclude another component but can further include another component, unless the context clearly dictates otherwise.

The word "exemplary" is used herein to mean "used as an example or an example" in the specification. Any embodiment described herein as "exemplary" is by no means necessarily to be interpreted as being preferred or having advantages over other embodiments.

As used in the present specification, the term "object" indicates an object to be tested, and should be detected by help of an electronic device disclosed in the present specification. Some non-restrictive examples of an object 110 may include products/goods (food, fruits, vegetables, etc.), liquid (water, alcoholic beverages, uranium, blood, salvia, etc.), and biological tissue (skin, muscle, osseous tissue, etc.).

Hereinafter, embodiments of the disclosure will be described in detail with reference to the accompanying drawings.

FIG. 1 is a schematic view showing determining state information about an object by using an electronic device according to an embodiment of the disclosure.

An electronic device 120 including an optical device 130 to acquire state information of an object 110 by using the optical device 130 is disclosed.

According to embodiments of the disclosure, the electronic device 120 may measure a light wavelength over a wide range of an electromagnetic spectrum by using the optical device 130. A spectrometer as an example of the electronic device 120 may be used for spectroscopic analysis of the object 110. Light emitted from a light source may be reflected from the object 110 and then transmitted, or the light may be absorbed in the object 110 or reflected from the object 110. A change generated while light emitted from the light source interacts with the object 110 may represent a characteristic of the object 110. Incident light reflected from the object 110 and entered the optical device 130 may be adjusted to a wavelength of interest by a dispersive element or a nondispersive element.

The electronic device 120 according to embodiments of the disclosure may include the optical device 130, and determine state information of the object 110 by analyzing the object 110 using the optical device 130 and at least one processor. The state information of the object 110 may include information about quality (freshness of food, determinations on a genuine and fake, degrees of cooking, ripeness, etc.) of a product/goods, information about a detected state (oxygenation, hydration levels, etc.) of biological tissue, information about a health state of a user of the electronic device 120 or a patient, etc. Exemplary types of the optical device 130 will be described in detail with reference to FIGS. 4 to 6B.

Figure 2:
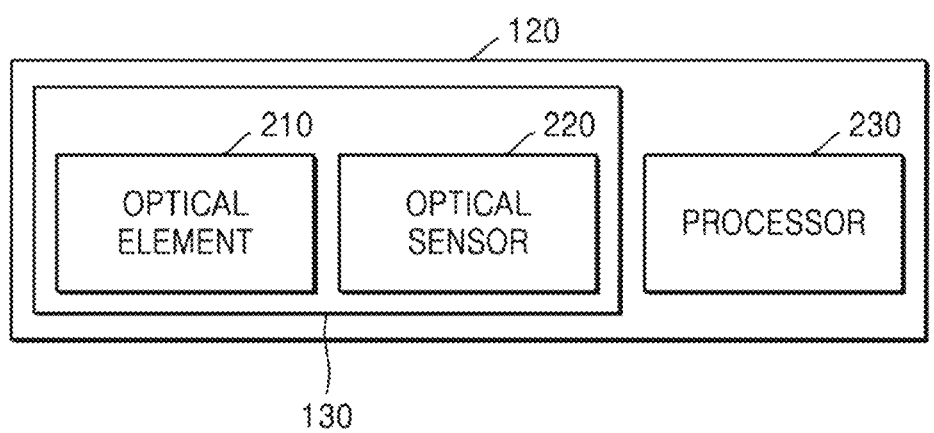
FIG. 2 shows a structure of an electronic device according to an embodiment of the disclosure.

FIG. 2 shows a structure of the electronic device according to an embodiment of the disclosure. The electronic device 120 according to an embodiment of the disclosure may include the optical device 130 including an optical element 210 and an optical sensor 220, and a processor 230.

The electronic device 120 according to embodiments of the disclosure may be implemented in various forms. The electronic device 120 may be implemented in a form of, for example, a general-purpose computer, a mobile device, a spectrometer, a refrigerator, a kiosk, etc. The mobile device may be implemented in a form of, for example, a smart phone, a tablet personal computer (PC), a wearable device, etc. The wearable device may be implemented in a form of glasses, a watch, clothes, shoes, an insert type biochip, a ring, etc.

The optical element 210 may be an optical device for changing a path of incident light. The optical element 210 according to embodiments of the disclosure may split incident light reflected from the object 110 into two or more incident light beams traveling along two or more light paths.

According to an embodiment, the optical element 210 may have a geometrical structure for splitting incident light into two or more incident light beams traveling along two or more light paths. According to another embodiment, the optical element 210 may include a combination of a plurality of optical devices for transmitting incident light to different light paths.

The optical sensor 220 may convert incident light into an electrical signal. The optical sensor 220 may detect the incident light split into the two or more incident light beams traveling along the two or more light paths by the optical element 210. According to an embodiment of the disclosure, the optical element 210 may include a plurality of sub sensors having different ranges of wavelengths. According to an embodiment of the disclosure, the different ranges of wavelengths may include at least one or a combination of an ultraviolet (UV) ray area, a visible (VIS) ray area, and a near-infrared ray (NIR) area. The plurality of sub sensors included in the optical sensor 220 may respectively correspond to at least some ranges of the different ranges of wavelengths. For example, the optical sensor 220 may include an ultraviolet ray detection sub sensor, a visible ray detection sub sensor, and a near-infrared ray detection sub sensor. According to an embodiment, at least one of the sub sensors may operate simultaneously to detect a wavelength of the ultraviolet ray area, the visible ray area, or the near-infrared ray area.

The processor 230 may control overall operations of the electronic device 120 and process data. The processor 230 may include one or more processors. The processor 230 may include one or more of a central processing unit (CPU), an application processor (AP), or a communication processor (CP).

The processor 230 may be implemented by using at least one of an application specific integrated circuits (ASICs), digital signal processors (DSPs), digital signal processing devices (DSPDs), programmable logic devices (PLDs), field programmable gate arrays (FPGAs), controllers, micro-controllers, microprocessors, and other electronic devices for performing functions.

According to an embodiment of the disclosure, the processor 230 may compare a first spectrum acquired from incident light reflected from the object 110 and detected by the optical sensor 220 to reference data (for example, a reference spectrum) to determine similarity, and determine state information of the object 110 based on the similarity. In this case, the reference spectrum may have been stored in a memory (not shown) of the electronic device 120 or an external device.

When the reference spectrum has been stored in the memory of the electronic device 120, the processor 230 may access the memory of the electronic device 120 to acquire the reference spectrum, and, when no reference spectrum has been stored in the memory of the electronic device 120, the processor 230 may request the external device to transmit reference data. According to an embodiment of the disclosure, the processor 230 may correspond to one or more processors that process reference data received from the external device.

According to an embodiment of the disclosure, the reference data may depend on a type of the object 110. For example, the reference data may be a complex form subject to Fourier transform and having a real part and an imaginary part, changes of an absorbance spectrum according to wavelengths, intensity changes of wavelengths over time, or a change amount of an absorbance spectrum for a specific wavelength over time.

According to an embodiment of the disclosure, the processor 230 may compare the first spectrum to the reference spectrum after performing Fourier transform on the first spectrum or without performing Fourier transform on the first spectrum, according to state information of the object 110 that a user of the electronic device 120 wants to know. In this case, two reference spectrums or more may be provided.

According to an embodiment of the disclosure, the state information of the object 110 may include information about quality (freshness of food, determinations on a genuine and fake, degrees of cooking, ripeness, etc.) of the object 110 (for example, a product/goods), information about a detected state (oxygenation, hydration levels, etc.) of biological tissue, information about a health state of a user of the electronic device 120 or a patient, etc. A detailed example of determining the state information of the object 110 will be described in detail with reference to FIGS. 9A to 15, later.

Although not shown in FIG. 2, the electronic device 120 may further include a communicator. The communicator may include one or more components enabling communication with another device. For example, the communicator may include at least one of a short-range communication module, a wired communication module, and a wireless communication module.

Figure 3:
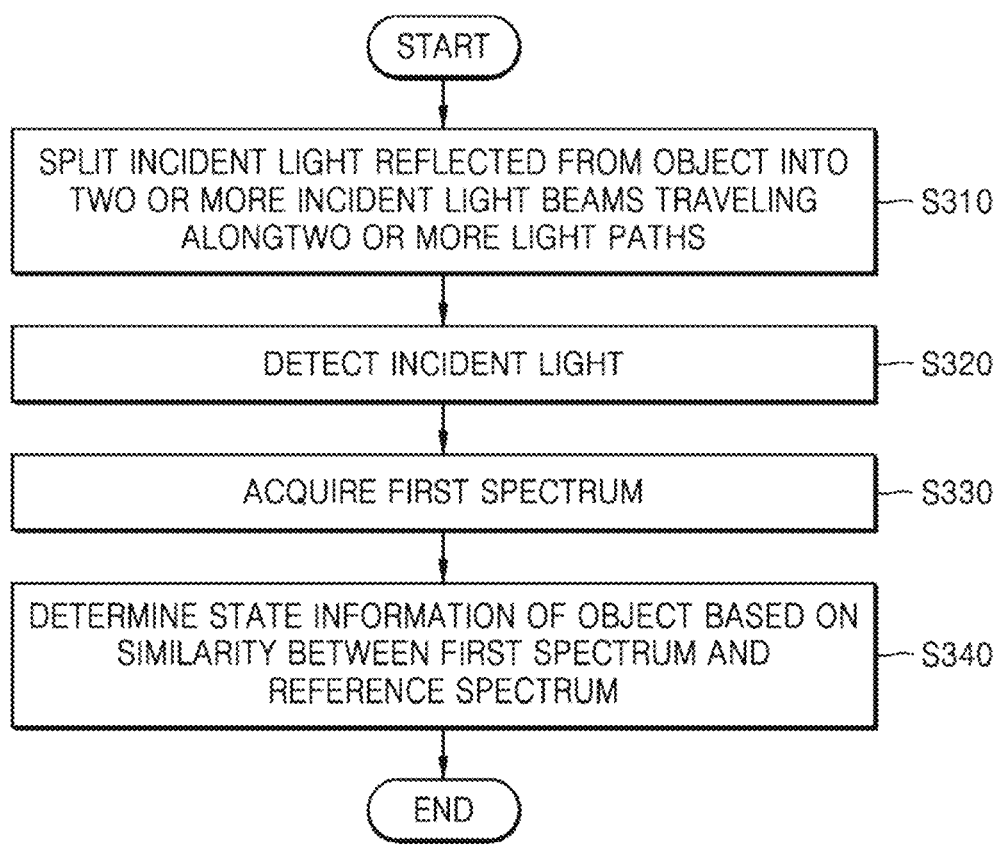
FIG. 3 is a flowchart showing an electronic device control method according to an embodiment of the disclosure.

FIG. 3 is a flowchart showing an electronic device control method according to an embodiment of the disclosure.

Individual operations of the electronic device control method according to the disclosure may be performed by various kinds of electronic devices including the optical element 210 for splitting incident light into a plurality of light beams traveling along a plurality of light paths, the optical sensor 220, and the processor 230. In the present specification, an embodiment in which the electronic device 120 (hereinafter, 120 is used as a reference numeral referring to electronic devices disclosed in the present specification) according to embodiments of the disclosure performs the electronic device control method will be described. Accordingly, embodiments described for the electronic device 120 may be applicable to the electronic device control method, and also, embodiments described for the electronic device control method may be applicable to the embodiments for the electronic device 120. The electronic device control method according to disclosed embodiments is not limited to being performed by the electronic device 120 disclosed in the present specification, and may be performed by various kinds of electronic devices.

The electronic device 120 may split incident light reflected from the object 110 into two or more incident light beams traveling along two or more light paths by using the optical element 210, in operation S310. According to an embodiment, a light source for irradiating light to the object 110 to acquire optical information from the object 110 may be used. The light source may be implemented in a form of an external device, or provided as a component of the electronic device 120.

According to an embodiment of the disclosure, incident light reflected from the object 110 may be collimated by a collimator before passing through the optical element 210. According to an embodiment of the disclosure, the collimator may be omitted.

According to an embodiment of the disclosure, the optical element 210 may split incident light reflected from the object 110 into two or more incident light beams traveling along two or more light paths, in operation S310. Then, the split incident light may be collected on a light receiving surface to form an interference area.

Then, the optical sensor 220 connected to the light receiving surface may detect the incident light reflected from the object 110, in operation S320.

Thereafter, the processor 230 may acquire a first spectrum from the detected incident light, in operation S330.

Then, the processor 230 may determine state information of the object 110 based on similarity between the first spectrum and a reference spectrum, in operation S340. According to an embodiment of the disclosure, a kind of the object 110 and the reference spectrum may depend on an input made on an application by a user using the electronic device 120. The user may input state information of the object 110 that he/she wants to know on the application. In this case, the processor 230 may access a memory (not shown) of the electronic device 120 or an external device based on the user's input made on the application to acquire information about a reference spectrum corresponding to a kind of the object 110. The user may input at least one of state information or an image of the object 110 that he/she wants to know to the electronic device 120 through the application. For example, when state information of the object 110 that the user of the electronic device 120 wants to know is information about whether the object 110 is a genuine product or a fake product, the user may input a command to check whether or not the object 110 is a genuine product, and an image of the object 110 photographed by a photographing device such as a camera capable of photographing the object 110. In this case, a kind of the object 110 may be a product, such as a watch and a bag, and the reference spectrum may correspond to a product of the same model and brand as the object 110 among the same kind of products as the object 110 input by the user.

Figure 4:
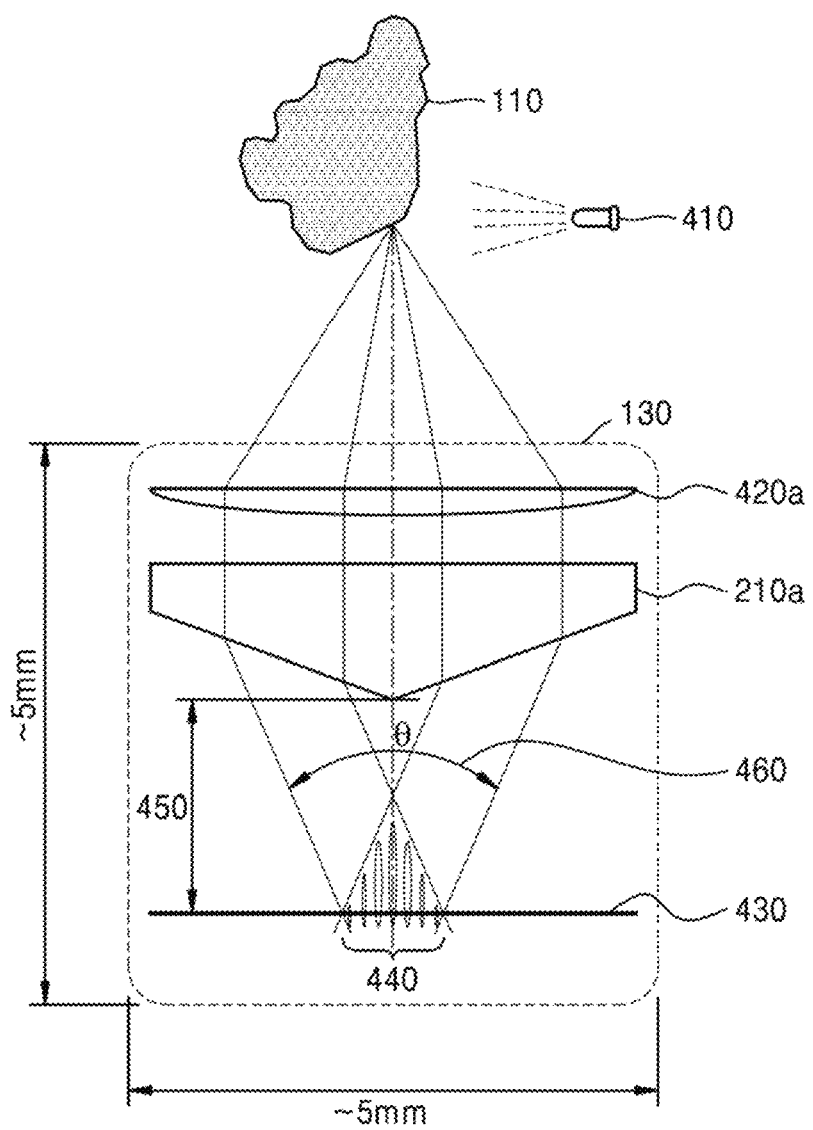
FIG. 4 shows a structure of an optical device according to an embodiment of the disclosure.

FIG. 4 shows a structure of an optical device according to an embodiment of the disclosure.

When a light source 410 irradiates light to the object 110, the light may be incident to the object 110, and the incident light may be reflected from the object 110. The light source 410 may be a natural light source such as the sun, or an artificial light source. The artificial light source may be an arbitrary kind of a light source made by a human, such as, for example, a flash lamp, a Light Emitting Diode (LED), a laser diode, a laser, etc. A kind of the light source 410 may depend on a purpose of use of the electronic device 120.

As shown in FIG. 4, the electronic device 120 may analyze a spectrum of the object 110 to which the light has been irradiated from the light source 410 to determine state information of the object 110. The light source 410 may be a natural light source such as the sun, or an artificial light source. The artificial light source may be an arbitrary kind of a light source made by a human, such as a flash lamp, a LED, a laser diode, a laser, etc. According to an embodiment of the disclosure, the light source 410 may be a flash or a LED mounted on a rear side of a smart phone or a front side of a smart TV. According to another embodiment of the disclosure, when battery power of a smart phone or a smart watch needs to be saved, the light source 410 may be provided outside the smart phone or the smart watch. A kind of the light source 410 may depend on a purpose of use of the electronic device 120. According to an embodiment of the disclosure, when the electronic device 120 is a smart phone and whether the object 110 is a genuine product is determined by using the smart phone, the light source 410 may be a flash lamp installed in the smart phone. According to another embodiment, when the electronic device 120 is a refrigerator and freshness of food is determined, the light source 410 may be a lighting installed in the refrigerator.

According to an embodiment of the disclosure, the electronic device 120 may change a wavelength range of the light source 410 according to at least one or a combination of a kind of the object 110 and a kind of state information acquired from the object 110. For example, when the object 110 is a solid, the light source 410 may irradiate light having a first range of wavelength, and, when the object 110 is a liquid, the light source 410 may irradiate light having a second range of wavelength which is different from the first range of wavelength. As another example, when content information of a component A is acquired from the object 110, the light source 410 may irradiate light having a third range of wavelength, and, when content information of a component B is acquired from the object 110, the light source 410 may irradiate light having a fourth range of wavelength that is different from the third range of wavelength.

According to an embodiment of the disclosure, as shown in FIG. 4, the optical device 130 may include a collimator 420a, an optical element 210a, and the optical sensor 220. According to an embodiment of the disclosure, the collimator 420a may be omitted.

The collimator 420a may convert a light path of incident light reflected from the object 110 to collimate the incident light.

According to an embodiment of the disclosure, the optical element 210a may split the light collimated by passing through the collimator 420a into two or more incident light beams traveling along two or more light paths. According to an embodiment of the disclosure, the optical element 210 of FIG. 2 may be the optical element 210a having a cone-shaped surface, and the optical element 210a may be in a form of an axicon which is a specialized type of lens.

According to an embodiment of the disclosure, the optical element 210a may be in a form of a modified axicon, for example, an axicon with a cut lower edge. Faces of the axicon through which the incident light reflected from the object 110 and then passed through the collimator 420a finally passes may respectively correspond to two or more light paths. The light paths of the incident light may change according to orientations of the faces of the axicon through which light passes and optical characteristics (for example, a refractive index) of the optical element 210a.

According to an embodiment of the disclosure, the collimator 420a and the optical element 210a may be positioned at fixed locations in the electronic device 120. By fixing the collimator 420a and the optical element 210a, pre-alignment or pre-adjustment of the optical device 130 may be not required, and accordingly, spectrum analysis of the object 110 may be accelerated.

Also, according to an embodiment of the disclosure, the collimator 420a and the optical element 210a may be coated with an antireflection coating to minimize optical loss.

The incident light passed through the optical element 210a may travel toward a light receiving surface 430 of the optical sensor 220 along different light paths from a plurality of surfaces of the optical element 210a. As shown in FIG. 4, the incident light beams traveling along two or more light paths may be incident to the light receiving surface 430 of the optical sensor 220. According to embodiments of the disclosure, the incident light beams traveling along the two or more light paths may interfere with each other at a predefined area. In this case, the different light paths may converge on the light receiving surface 430 to generate an interference fringe between the incident light beams. The area on the light receiving surface 430 of the optical sensor 430, at which interference occurs between the incident light beams traveling along the two or more light paths, is referred to as an interference area 440.

A size of the optical device 130 may be determined based on a size of the optical element 210a, a separation distance 450 between the optical element 210a and the light receiving surface 430, a size of the collimator 420a, etc. The separation distance 450 may represent a distance between a predefined reference point of the optical element 210a and a predetermined reference point of the optical sensor 220. For example, the separation distance 450 may be defined as a distance between a lowest location of the optical element 210a and the light receiving surface 430 of the optical sensor 220. The optical device 130 according to an embodiment may have horizontal, vertical, and height lengths of 5 mm. According to an embodiment of the disclosure, θ 460 may be an angle between the different light paths. According to an embodiment of the disclosure, a size of θ 460 and the separation distance 450 may be determined to detect the interference area 440 where interference between the incident light beams of two or more paths occurs from the light receiving surface 430 of the optical sensor 220. The interference fringe between the incident light beams of the two or more paths may be detected from the interference area 440. The collimator 420a and the optical element 210a may be fixed.

According to an embodiment of the disclosure, a wavelength range that is detectable by the optical device 130, and resolution of the optical device 130 may be calculated. For example, the optical sensor 220 may have a pixel size of 1.12 μm and a total pixel number of 4656×3496. In this case, 5 pixels may be required for each interference fringe to appropriately detect incident light. Accordingly, an interference fringe may have a period of minimally 5 pixels*1.12 um to 6 um. When a period of an interference fringe is 6 um, θ 460≈5.7°. In this case, a wavelength range that is detectable by the optical device 130 may be 400 nm to 900 nm, and resolution of the optical device 130 may be 1 nm.

Figure 5:
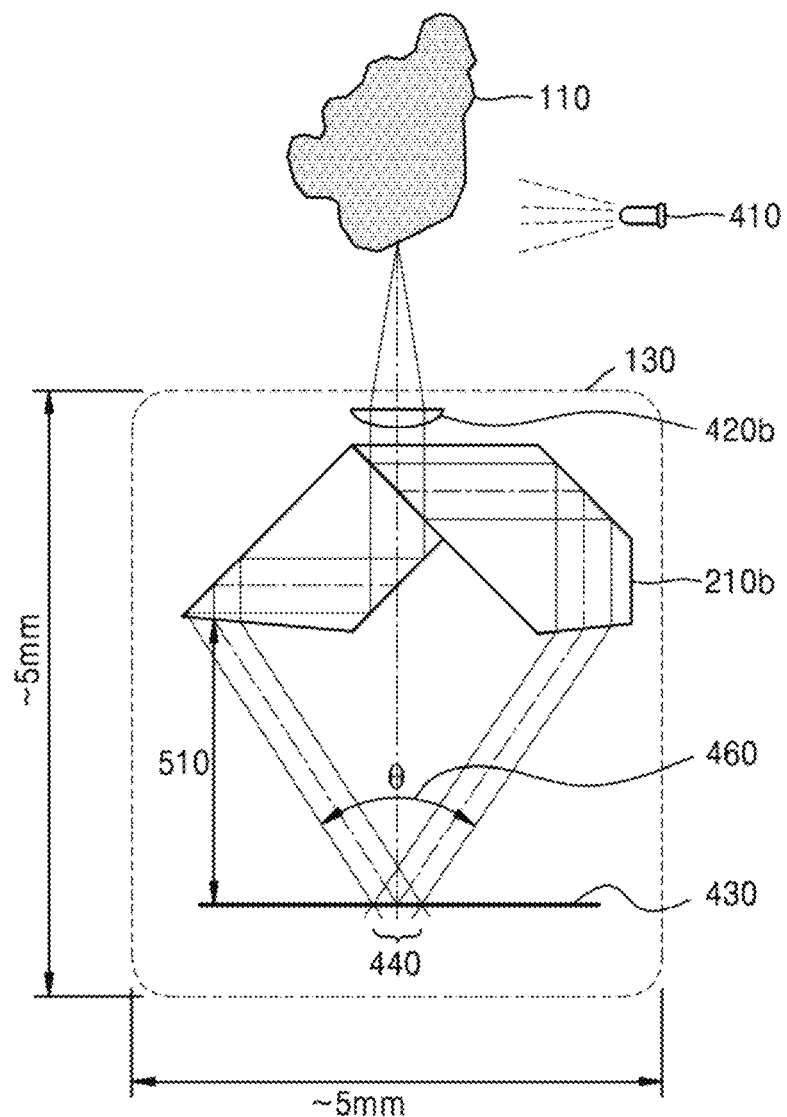
FIG. 5 shows another structure of an optical device according to an embodiment of the disclosure.

FIG. 5 shows another structure of an optical device according to an embodiment of the disclosure.

As shown in FIG. 5, a collimator 420b may collimate incident light reflected from the object 110. According to an embodiment, the collimator 420b may be omitted.

According to an embodiment of the disclosure, the optical element 210 of FIG. 2 may be an optical element 210b including a plurality of prisms respectively corresponding to two or more light paths. Each of the plurality of prisms may have a 3Dimensional (3D) structure of various shapes, and for example, each prism may be in a shape of a polyhedron having faces of a quadrangle, a pentagon, etc. The plurality of prisms may be integrated into one body or formed by bonding unit prisms. The number of the prisms may be determined variously according to embodiments. For example, the number of the prisms may be determined according to the number of light paths that need to be generated by splitting incident light. Also, shapes, orientations, structures, etc. of the plurality of prisms may be configured such that incident light entered the optical element 210 is split into two or more incident light beams traveling along two or more light paths and then collected accurately on the interference area of the light receiving surface 430. In FIG. 5, two prisms are shown of which one faces are in contact with each other, although not limited thereto.

According to an embodiment of the disclosure, a separation distance 510 may represent a distance between a predefined reference point of the optical element 210b and a predefined reference point of the optical sensor 220. For example, the separation distance 510 may be defined as a distance between a lowest location of the optical element 210b and the light receiving surface 430 of the optical sensor 220. In this case, the separation distance 510 may be determined to detect an interference area where interference between incident light beams of two or more paths occurs from the light receiving surface 430 of the optical sensor 220. Also, the separation distance 510 may be determined to detect an interference area having a predefined size or more from the light receiving surface 430. An interference fringe between the incident light beams of the two or more paths may be detected from the interference area. The collimator 420b and the optical element 210b may be fixed.

Although not shown in FIGS. 4 and 5, the electronic device 120 may further include a memory, the processor 230, and a display. The memory may store data including a plurality of reference spectrums. Each reference spectrum may correspond to a specific object type as discussed above. The processor 230 may be connected to the optical sensor 220 to acquire a first spectrum, and access the memory to select a reference spectrum corresponding to the same type as the object 110 and determine whether the first spectrum matches the reference spectrum. The display may display a result of the determination.

The optical device 130 may function as a spectrometer, and be included in a mobile device, such as a smart phone or a smart watch. The embodiments of the disclosure may include the optical device 130 having a small size for acquiring optical information from the object 110 in a small-sized mobile device including the memory, the processor 230, the display, etc. to enable the small-sized mobile device to easily and quickly acquire state information of the object 110.

Figure 6A:
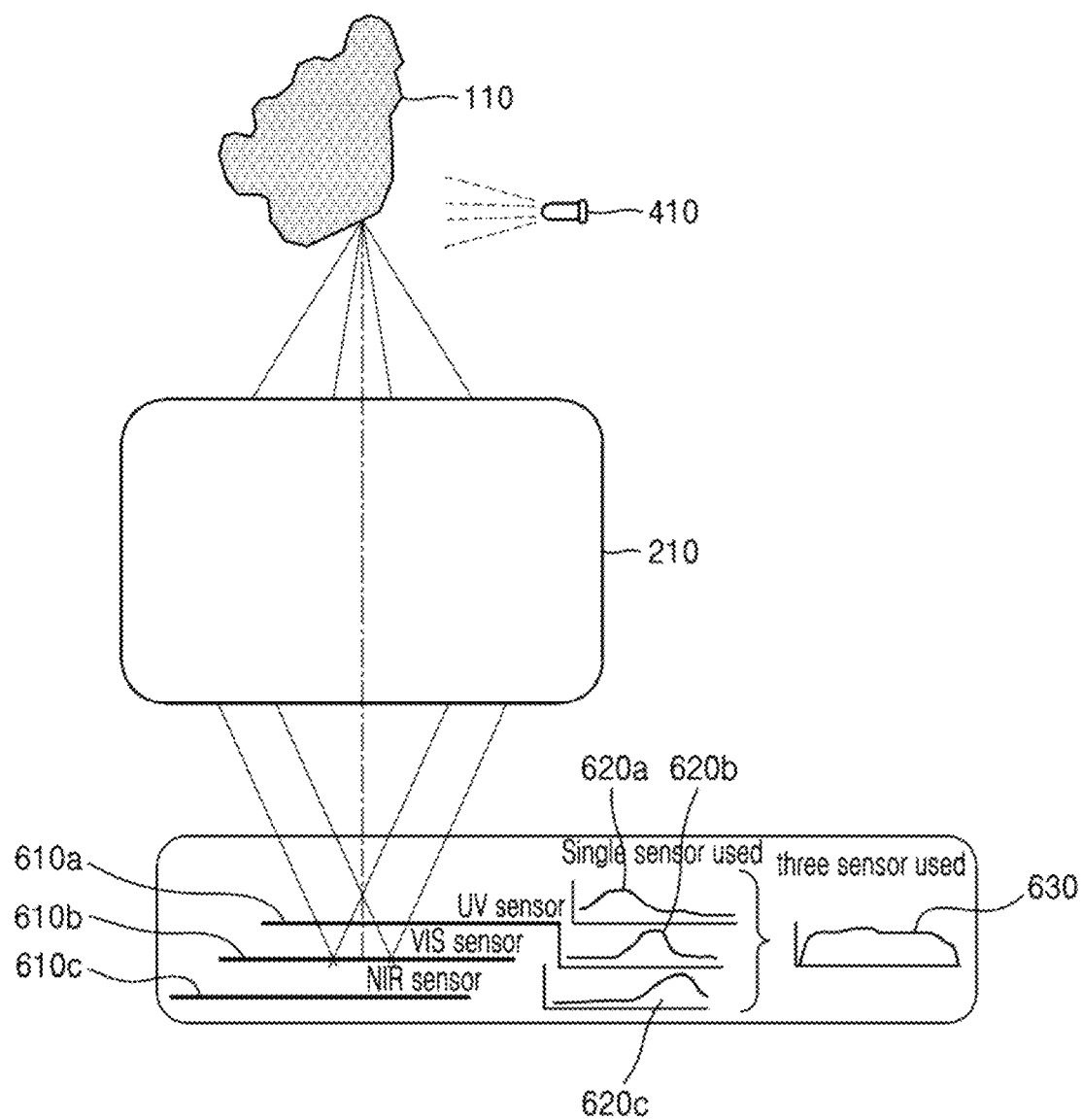
FIG. 6A shows wavelength ranges detected by optical sensors of an optical device according to an embodiment of the disclosure.

FIG. 6A shows wavelength ranges detected by optical sensors of an optical device according to an embodiment of the disclosure.

According to an embodiment of the disclosure, the optical element 210a or 210b may enable the optical sensor 220 to detect the interference area 440 between the incident light beams reflected from the object 110.

As shown in FIG. 6A, the optical sensor 220 may include a plurality of sub sensors to respectively detect spectrums in different ranges of wavelengths. The plurality of sub sensors may include a first sensor 610a capable of detecting a spectrum of an ultraviolet (UV) ray wavelength range, a second sensor 610b capable of detecting a spectrum of a visible (VIS) ray wavelength range, and a third sensor 610c capable of detecting a spectrum of a near-infrared ray (NIR) wavelength range. According to an embodiment of the disclosure, the optical sensor 220 may include at least one sub sensor of the first to third sensors 610a to 610c, and the sub sensors 610a, 610b, and 610c may respectively detect spectrums of different wavelength ranges. According to an embodiment of the disclosure, the first sensor 610a may detect a spectrum of a wavelength range of 300 nm to 500 nm, the second sensor 610b may detect a spectrum of a wavelength range of 400 nm to 750 nm, and the third sensor 610c may detect a spectrum of a wavelength range of 750 nm to 1000 nm.

A graph 620a may represent an absorbance spectrum of the first sensor 610a, a graph 620b may represent an absorbance spectrum of the second sensor 610b, and a graph 620c may represent an absorbance spectrum of the third sensor 610c. According to an embodiment of the disclosure, because the optical sensor 220 includes at least one sub sensor of the first to third sensors 610a to 610c, a spectrum corresponding to all wavelength ranges detected by the individual sub sensors, as shown in a graph 630, may be detected. The optical sensor 220 may obtain an absorbance spectrum of a wide wavelength range, as shown in the graph 630, by using all of the first sensor 610a, the second sensor 610b, and the third sensor 610c.

Figure 6B:
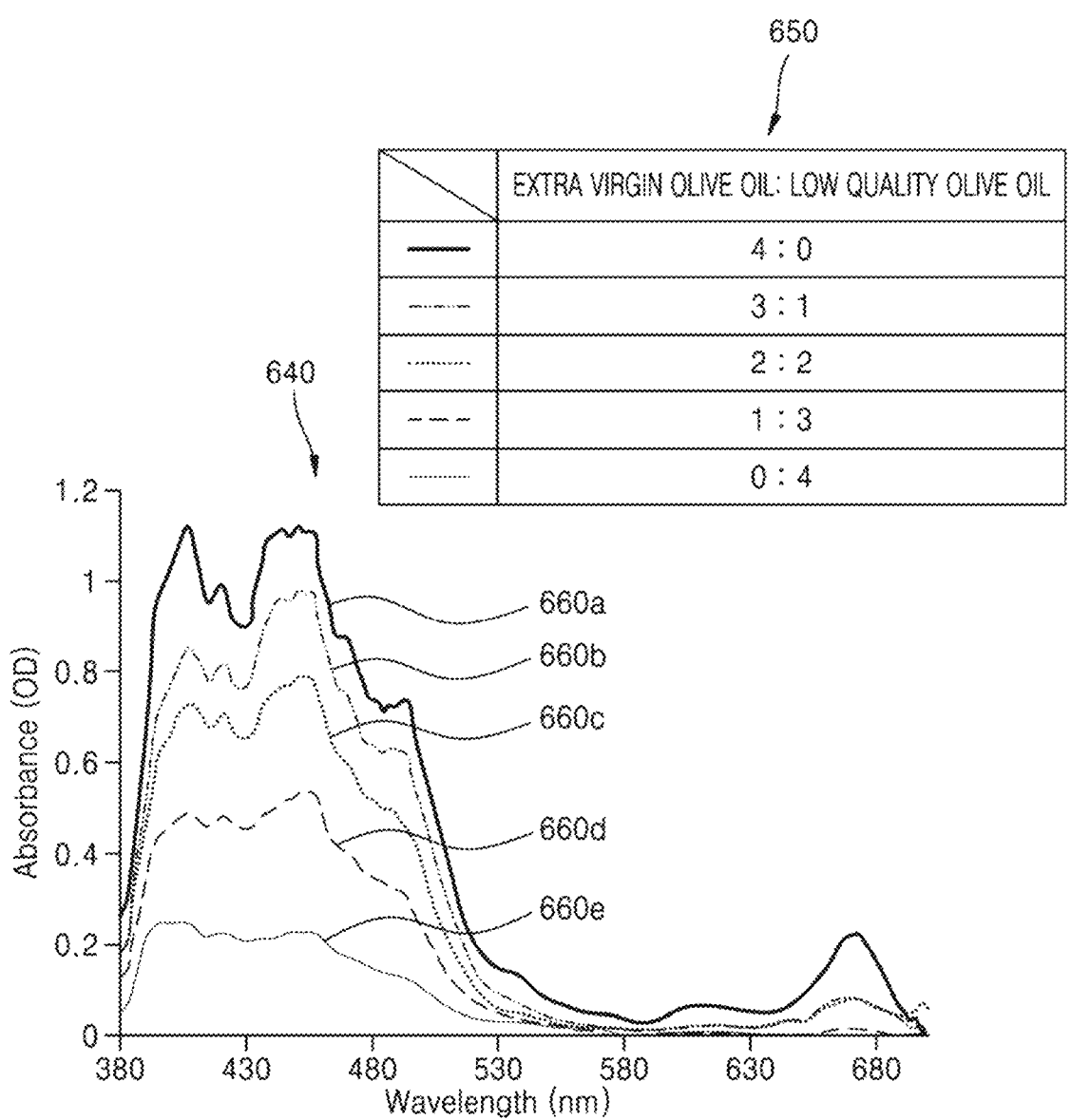
FIG. 6B shows absorbance spectrums of olive oil mixtures at different mixing ratios of different olive oils, the absorbance spectrums being detected by an optical sensor of an electronic device according to the disclosure.

FIG. 6B shows absorbance spectrums of olive oil mixtures mixed at different mixing ratios of different olive oils, the absorbance spectrums detected by an optical sensor of an electronic device according to the disclosure.

A graph 640 shows absorbance spectrums of olive oil mixtures according to wavelengths, mixed at different mixing ratios of Extra Virgin Olive Oil and low-quality olive oil, the absorbance spectrums detected by the optical sensor 220. A table 650 represents mixing ratios of the low-quality olive oil with respect to the Extra Virgin Olive Oil. As shown in FIG. 6B, the absorbance spectrums 660a to 660e of the graph 640 may respectively correspond to the detected absorbance spectrums of the olive oil mixtures mixed at the different mixing ratios (for example, 4:0, 3:1, 2:2, 1:3, and 0:4) of the low-quality olive oil with respect to the Extra Virgin Olive Oil. According to an embodiment of the disclosure, the graph 640 shows a detected wavelength range of about 380 nm to about 680 nm, and the wavelength range may be included in a wavelength range detected by the first sensor 610a and the second sensor 610b. According to an embodiment of the disclosure, the processor 230 may compare the absorbance spectrums 660a to 660e between a wavelength of about 380 nm and a wavelength of about 530 nm to determine quality of olive oil. In this case, when the processor 230 compares only absorbance spectrums 660a to 660e detected by the second sensor 610a, the processor 230 may have difficulties in accurately determining the quality of the olive oil. However, when the processor 230 compares absorbance spectrums 660a to 660e detected by the first sensor 610a and the second sensor 610b, the processor 230 may more accurately determine the quality of the olive oil.

Figure 7:
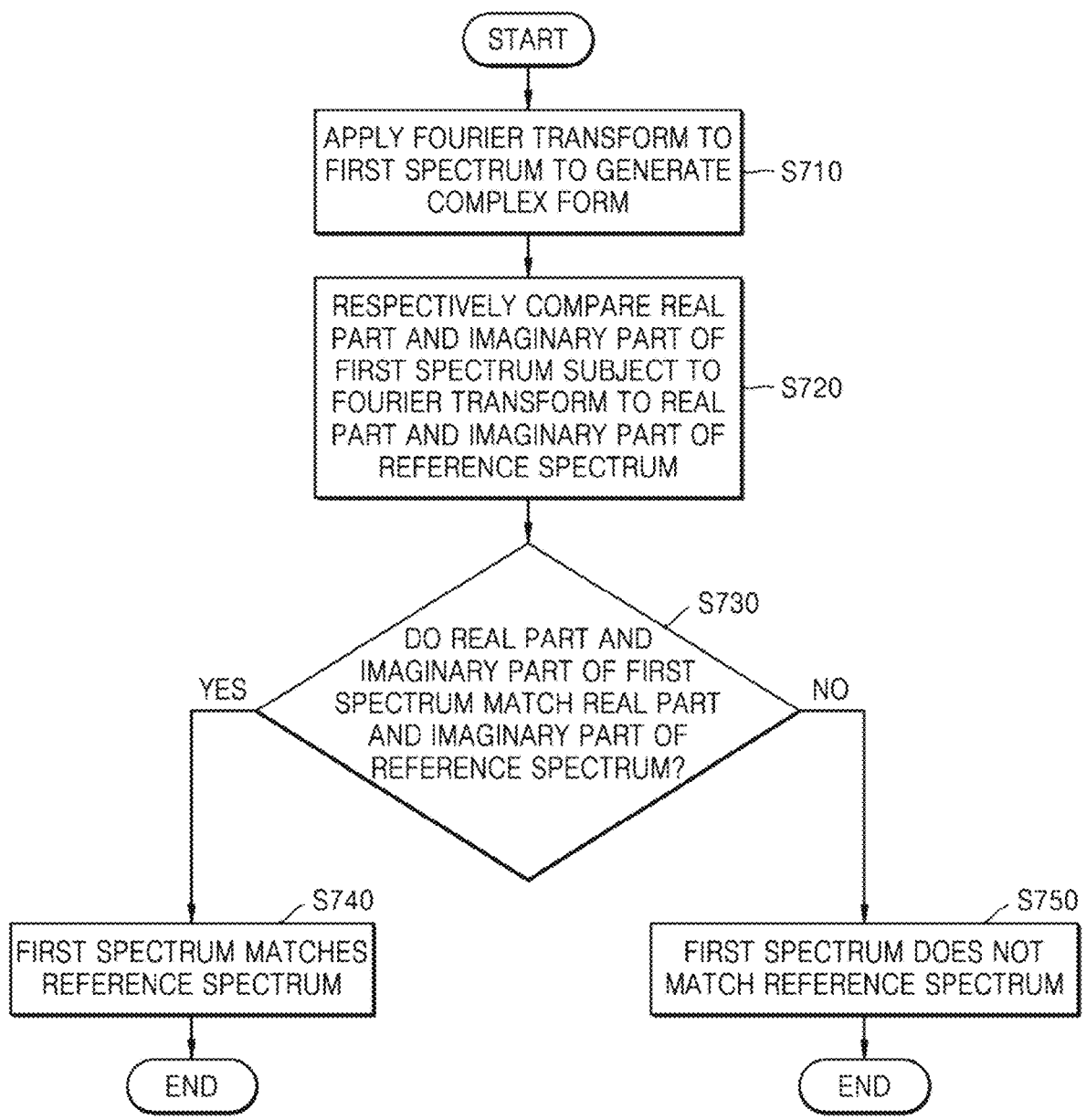
FIG. 7 is a flowchart showing a process of determining the similarity between a first spectrum and a reference spectrum, according to an embodiment of the disclosure.

FIG. 7 is a flowchart showing a process of determining similarity between a first spectrum and a reference spectrum, according to an embodiment of the disclosure.

A process of acquiring a first spectrum has been described above through operations S310 to S330 of FIG. 3. According to an embodiment of the disclosure, the processor 230 may apply Fourier transform to the first spectrum to generate a complex form including a real part and an imaginary part, in operation S710. The real part and the imaginary part may respectively correspond to amplitude information (or an amplitude spectrum) and phase information (or a phase spectrum). Fourier transform is well known to those skilled in the art, and therefore, descriptions thereof will be omitted in the present specification.

Then, the processor 230 may compare the real part and imaginary part of the first spectrum subject to Fourier transform to a real part and an imaginary part of a reference spectrum, respectively, in operation S720.

Then, the processor 230 may determine whether the real part and imaginary part of the first spectrum respectively match the real part and imaginary part of the reference spectrum, based on similarity between the first spectrum and the reference spectrum, in operation S730. Similarity means a degree of matching between two or more objects to be compared. The processor 230 may determine similarity through convolution, a determination on a difference after normalization, pattern matching, etc. According to an embodiment of the disclosure, determining that two compared spectrums match each other may not require complete overlapping of the two spectrums, and, when changes of the two spectrums match each other by a predefined degree or more, it may be determined that the two spectrums match each other. That the changes of the two spectrums match each other by the predefined degree or more means a case in which inclinations or inflection points of the spectrums match each other by a predefined level or more, a case in which convolution result values are greater than or equal to a predefined value, etc. According to an embodiment of the disclosure, when the processor 230 determines that similarity is greater than or equal to a predefined level, the processor 230 may determine that compared objects match each other, and otherwise, the processor 230 may determine that the compared objects do not match each other.

Then, when the processor 230 determines that the real part and imaginary part of the first spectrum subject to Fourier transform respectively match the real part and imaginary part of the reference spectrum based on the similarity, the processor 230 may determine that the first spectrum matches the reference spectrum, in operation S740, and, when the processor 230 determines that any one of the real part and imaginary part of the first spectrum does not match the corresponding one of the real part and imaginary part of the reference spectrum, the processor 230 may determine that the first spectrum does not match the reference spectrum, in operation S750.

Figure 8:
FIG. 8 shows a result of a determination on matching between a first spectrum and a reference spectrum based on similarity according to an embodiment of the disclosure.

FIG. 8 shows a result of a determination on matching between a first spectrum and a reference spectrum based on similarity according to an embodiment of the disclosure. As described above, the first spectrum and the reference spectrum may be subject to Fourier transform to each become a complex form having a real part and an imaginary part. In this case, the real part and the imaginary part may respectively correspond to amplitude information (or an amplitude spectrum) and phase information (or a phase spectrum). As shown in FIG. 8, according to an embodiment of the disclosure, a solid line 810 represents a Fourier-transformed form of the reference spectrum, and a dotted line 820 represents a Fourier-transformed form of the first spectrum. In this case, the reference spectrum is not necessarily a spectrum, and two or more reference spectrums may be provided. When the processor 230 determines that a real part and imaginary part of the Fourier-transformed first spectrum respectively match a real part and imaginary part of the Fourier-transformed reference spectrum, the processor 230 may determine that the first spectrum matches the reference spectrum (830), and, when the processor 230 determines that any one of the real part and imaginary part of the Fourier-transformed first spectrum does not match the corresponding one of the real part and imaginary part of the Fourier-transformed reference spectrum, the processor 230 may determine that the first spectrum does not match the reference spectrum (840)

Figure 9A:
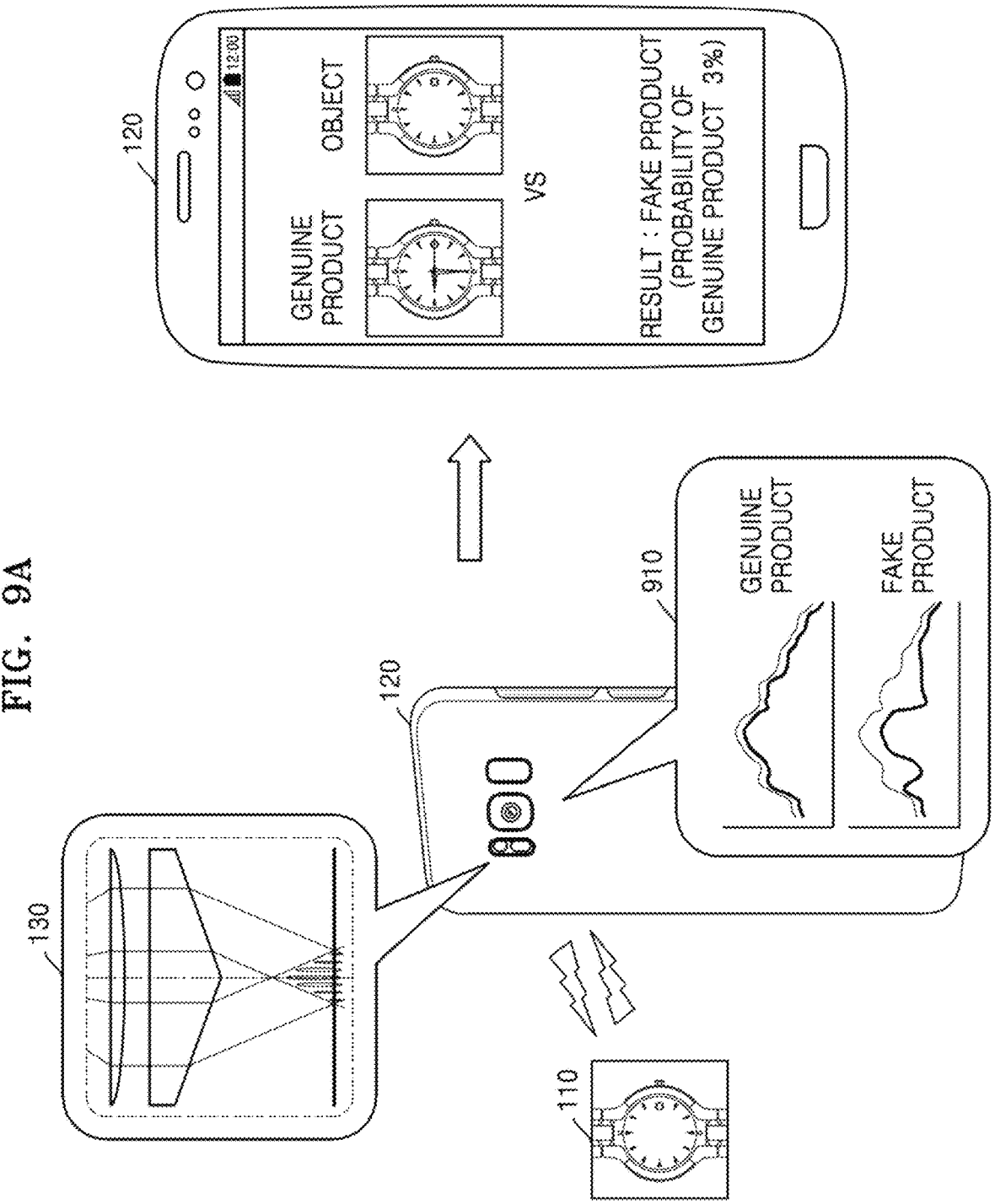
FIG. 9A shows an operation of an electronic device according to an embodiment of the disclosure.

FIG. 9A shows an operation of an electronic device according to an embodiment of the disclosure.

According to an embodiment of the disclosure, the electronic device 120 may determine whether or not the object 110 is a genuine product. According to an embodiment of the disclosure, when a user of the electronic device 120 inputs a command for checking whether or not the object 110 is a genuine product on an application or the user executes a mode for identifying a genuine product, the processor 230 may prepare to identify a genuine product. Then, the processor 230 may display a message requesting the user to input an image for the object 110 to be determined to be a genuine product or not. Then, the user may photograph the object 110 by using a photographing device (not shown) to input a photographed image to the electronic device 120 on the application. The photographed image may be photographed by a photographing device installed in the electronic device 120, or photographed by a photographing device that is separated from the electronic device 120 and then transmitted to the electronic device 120. According to another embodiment of the disclosure, the user may input his/her intention informing that he/she wants to check whether or not the object 110 is a genuine product, and a photographed image of the object 110, before the processor 230 displays the message requesting the user to input the photographed image. Thereafter, when a first spectrum for the object 110 is input to the electronic device 120 through the optical device 130, the processor 230 may access the memory to acquire a reference spectrum corresponding to a genuine product of the same type as the object 110. In this case, the type of the object 110 may be a product, such as, for example, a watch, a bag, shoes, etc., to be determined to be a genuine product or not. Thereafter, the processor 230 may determine whether or not the object 110 is a genuine product based on similarity through a series of processes shown in FIG. 7.

A block 910 shows a result of a determination on matching based on similarity by the processor 230 as shown in FIG. 8. According to an embodiment of the disclosure, when the first spectrum does not match the reference spectrum so that the object 110 is determined to be a fake product, the processor 230 may calculate a probability that the object 110 will be a genuine product based on similarity, and show a result of the determination about whether the object 110 is a genuine product together with the probability that the object 110 will be a genuine product, for the user, through a screen of the electronic device 120.

According to an embodiment of the disclosure, the object 110 may be a watch. In this case, when the user inputs his/her intention informing that he/she wants to check whether the watch is a genuine product and a photographed image of the watch to be determined to be a genuine product or not, the processor 230 may determine whether or not the watch is a genuine product, calculate a probability that the watch will be a genuine product, and show a result of the determination on whether or not the watch is a genuine product together with the probability that the watch will be a genuine product, for the user, through the screen of the electronic device 120, as shown in FIG. 9A.

According to another embodiment of the disclosure, there may be a case in which the user of the electronic device 120 wants to check ripeness, a degree of cooking, etc. of the object 110. In this case, a type of the object 110 may be food, such as, for example, fruit, fish, or meat.

Figure 9B:
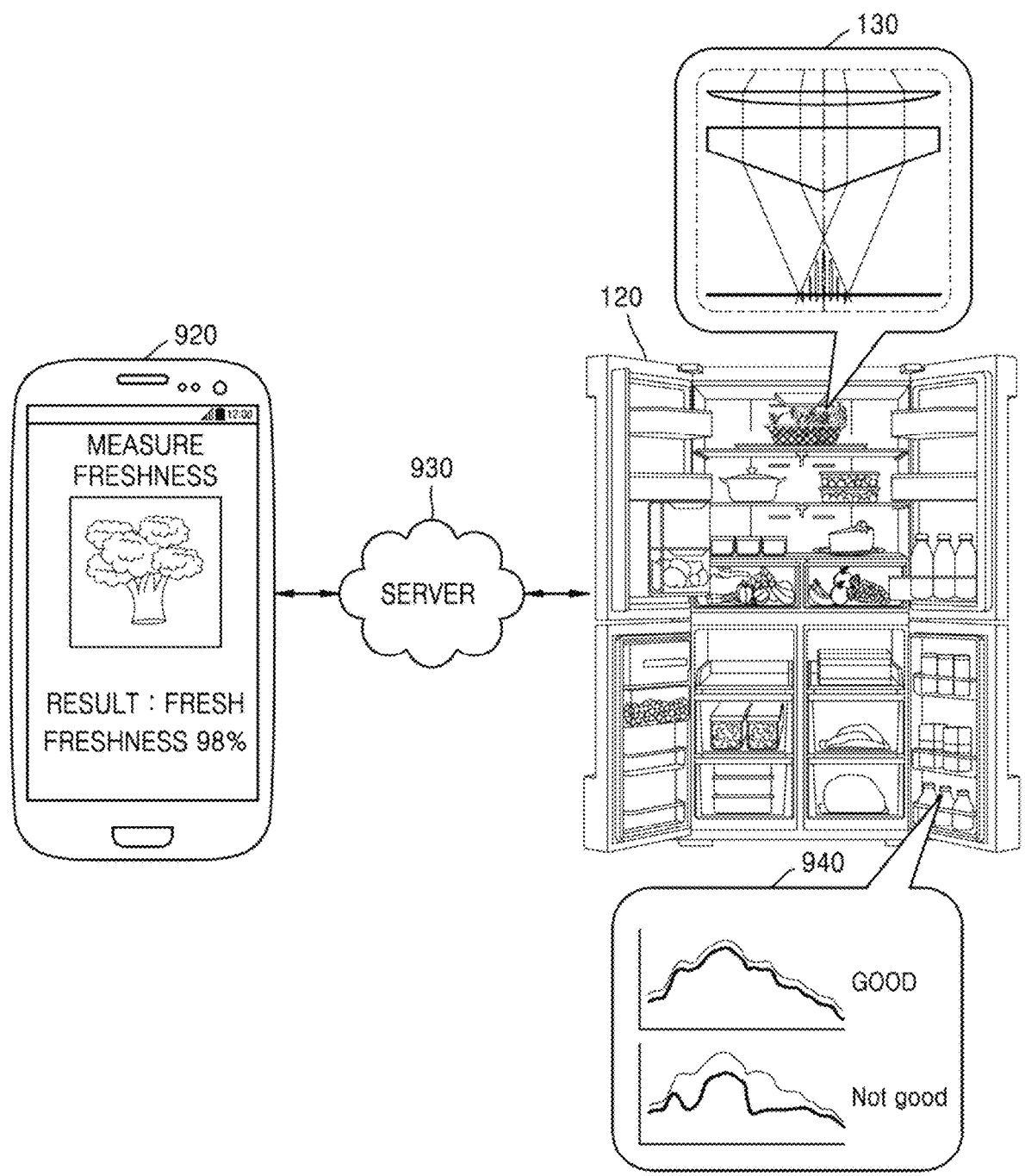
FIG. 9B shows an operation of an electronic device according to an embodiment of the disclosure.

FIG. 9B shows an operation of an electronic device according to an embodiment of the disclosure.

According to an embodiment of the disclosure, the electronic device 120 may determine state information of the object 110, and a first external device 920 that is separated from the electronic device 120 may show a result of the determination for a user. However, the electronic device 120 may show the determined result of the state information of the object 110 through a screen installed on the electronic device 120, not via the first external device 920.

According to an embodiment of the disclosure, an application that the user uses may be installed in at least one of the first external device 920 or the electronic device 120. When the first external device 920 is provided, the processor 230 may interact with the first external device 920 through a server 930.

According to an embodiment of the disclosure, when the user of the electronic device 120 wants to determine state information of the object 110, the user may input his/her intention informing that he/she wants to determine state information of the object 110 through input means (for example, through a touch when the screen is a touch screen) of the electronic device 120. However, when the user of the first external device 920 inputs his/her intention informing that he/she wants to determine state information of the object 110 through an application of the first external device 920, the first external device 920 may transmit a request for determining state information of the object 110 to the electronic device 120 through the server 930. Thereafter, the processor 230 may determine state information of the object 110 based on similarity between a first spectrum and a reference spectrum, through the process shown in FIG. 7, and transmit result data to the first external device 920 through the server 930.

A block 940 shows an example of a result of a determination on similarity by the processor 230, as shown in FIG. 8. According to an embodiment of the disclosure, when the first external device 920 is provided, a user may see determined state information of the object 110 through a screen of the first external device 920, and, when no first external device 920 is provided, the user may see determined state information of the object 110 through a screen of the electronic device 120.

According to an embodiment of the disclosure, the electronic device 120 may be a refrigerator, state information of the object 110 may be freshness of food, and the object 110 may be broccoli. In this case, a type of the object 110 may be food. When the user inputs his/her intention informing that he/she wants to check freshness of broccoli through an application of the first external device 920 or the electronic device 120, the processor 230 may determine whether or not the broccoli is fresh and freshness of the broccoli based on similarity, as shown in the block 940. Then, the processor 230 may transmit result data of the determination to the first external device 920, and the first external device 920 may show whether or not the broccoli is fresh and freshness of the broccoli through the screen based on the result data of the determination. According to an embodiment of the disclosure, the processor 120 may show the result data of the determination directly through the screen of the electronic device 120.

Figure 10:
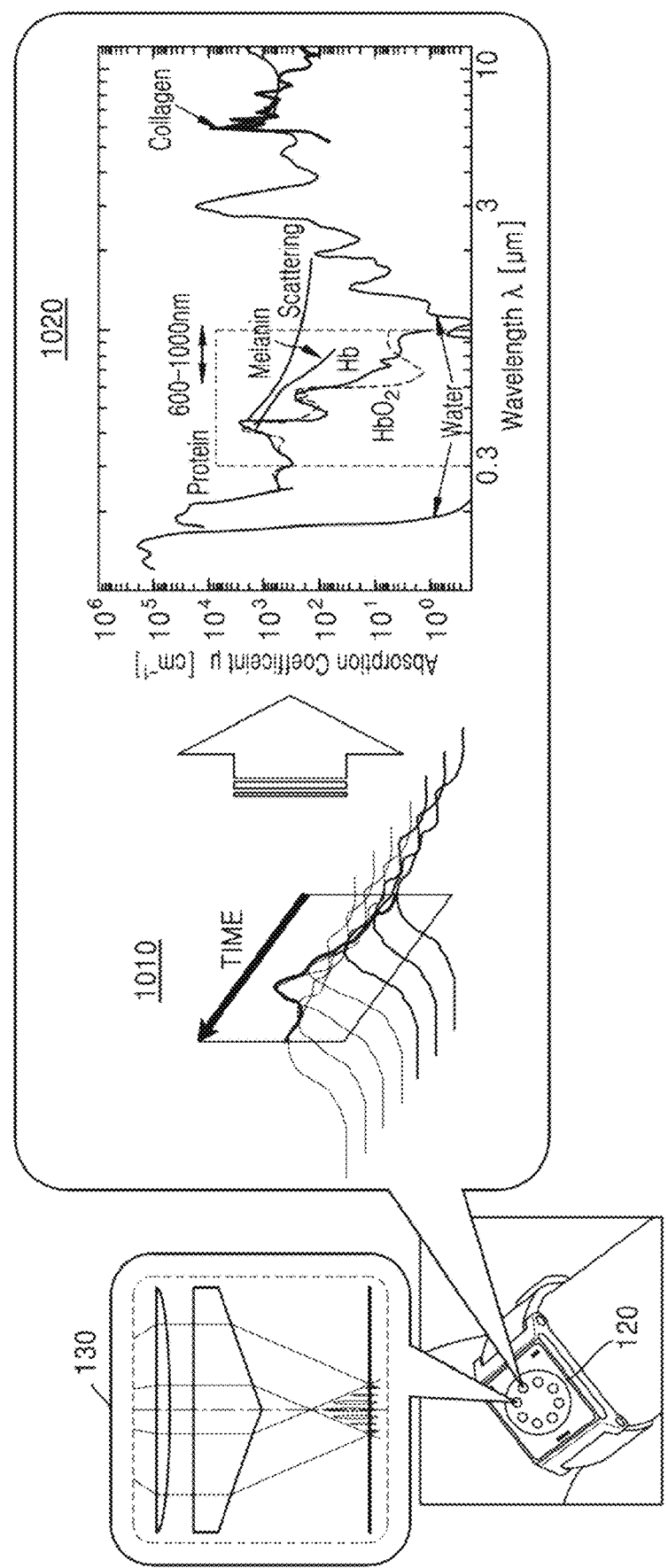
FIG. 10 shows results obtained by measuring spectrums of incident light reflected from an object over time, according to an embodiment of the disclosure.

FIG. 10 shows results obtained by measuring spectrums of incident light reflected from an object over time, according to an embodiment of the disclosure.

As shown in FIG. 10, the electronic device 120 may be a wearable smart watch, and the optical device 130 may be small enough to be installed in the smart watch. According to an embodiment of the disclosure, as shown in a graph 1010, a plurality of spectrums may be acquired at the same time by using the electronic device 120. Then, the processor 230 may apply Fourier transform to the acquired spectrums to acquire absorption coefficients according to wavelengths for individual materials, as shown in the graph 1020.

According to an embodiment, an object may be a predefined component contained in a user's skin, and the electronic device 120 may detect a change of a portion of the predefined component contained in the user's skin over time to acquire information about the user's health state. For example, the predefined component may be at least one of melanin, protein, hemoglobin, oxidized hemoglobin, water, or collagen, or a combination thereof. The electronic device 120 may acquire information about an amount of the predefined component at regular intervals or when a predefined condition is fulfilled. For example, when a user's heart rate is greater than or equal to a predefined value, the electronic device 120 may acquire information about an amount of the predefined component. According to another example, the electronic device 120 may acquire information about an amount of the predefined component whenever a count of a passometer worn on a user increases by a predefined number.

FIG. 11 shows an example of determining state information of an object in an electronic device according to an embodiment of the disclosure.

According to an embodiment of the disclosure, the object 110 may be oil, and reference objects may be first reference oil and second reference oil. The processor 230 may perform Fourier transform on a spectrum for the oil which is the object 110, and determine matching and a degree of matching with reference data corresponding to the first reference oil and the second reference oil. As shown in FIG. 11, a graph 1110 shows amplitude information of an absorbance spectrum of the object 110, acquired by applying Fourier transform, amplitude information of an absorbance spectrum of the first reference oil, and amplitude information of an absorbance spectrum of the second reference oil. A graph 1120 shows phase information of the absorbance spectrum of the object 110, phase information of the absorbance spectrum of the first reference oil, and phase information of the absorbance spectrum of the second reference oil. In the case of oil, it may be difficult to determine which one of the reference oil is similar to the object 110 only through comparison of the amplitude information shown in the graph 1110. However, as shown in the graph 1120, by comparing the phase information of the object 110 to the phase information of the reference oils, it may be determined that the phase information of the object 110 matches the phase information of the second reference oil. Accordingly, the processor 230 may determine that the object 110 matches the second reference oil, not the first reference oil, based on similarity, and calculate a degree of matching, through the process shown in FIG. 7. Accordingly, according to the current embodiment, by comparing the amplitude information and the phase information together, more accurate state information of the object 110 may be acquired.

The state information of the object 110 may depend on a purpose of an application that a user uses. According to an embodiment of the disclosure, the state information of the object 110 may be quality of oil, and reference objects may be low-quality oil and high-quality oil, or oil having quality of a specific level or more. According to an embodiment of the disclosure, the state information of the object 110 may be a degree of denaturalization of a product, and the reference objects may be oil when it is a short time after the oil is produced and oil when it is a long time after the oil is produced, or oil when it is a predefined time after the oil is produced as the same product as the object 110.

Figure 12:
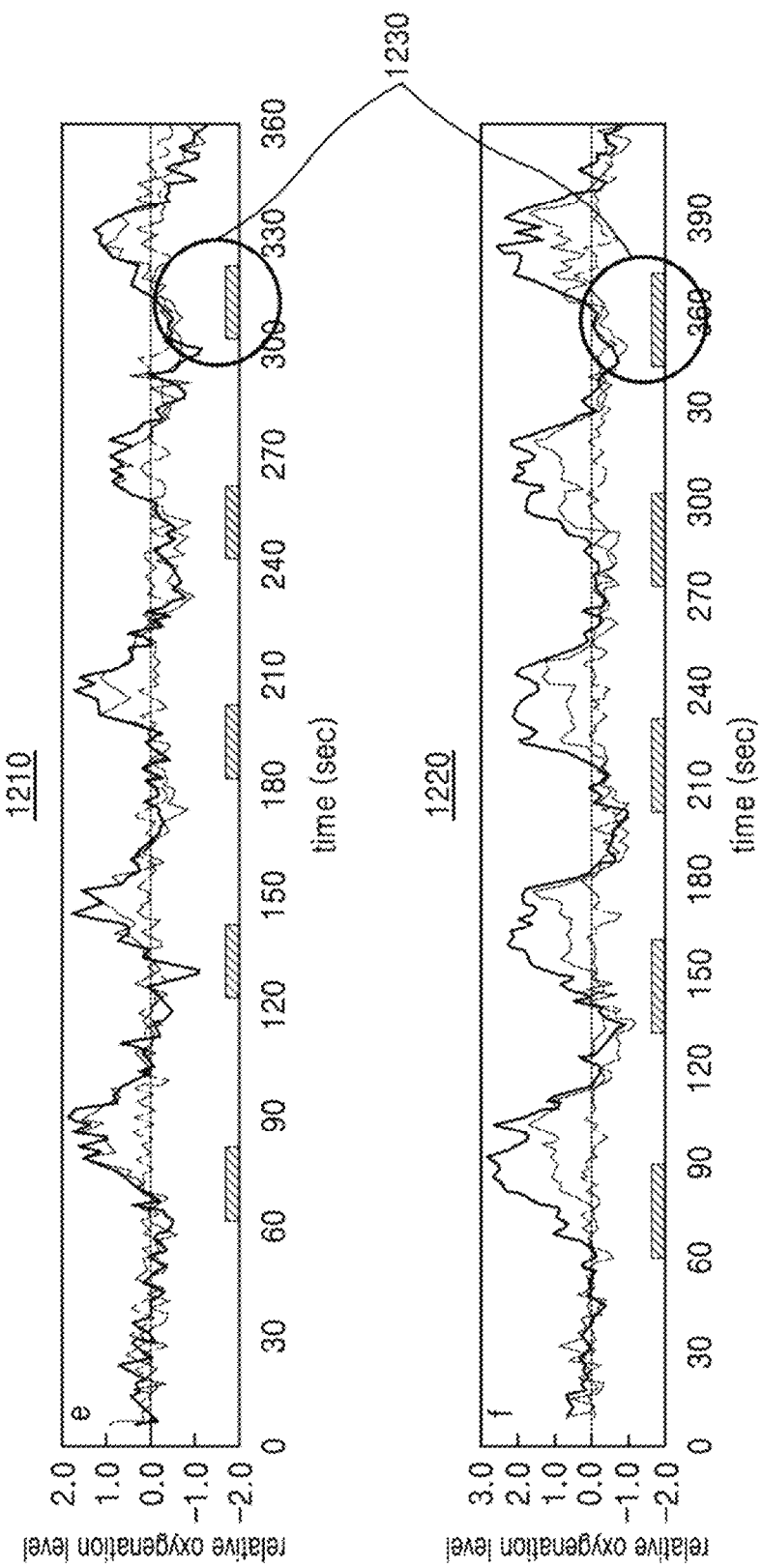
FIG. 12 shows an example of determining state information about an object in an electronic device according to an embodiment of the disclosure.

FIG. 12 shows an example of determining state information of an object in an electronic device according to an embodiment of the disclosure.

According to an embodiment of the disclosure, the electronic device 120 may measure a change of an oxygenation level (or oxygen saturation) of blood in a specific breath interruption time 1230 over time. In this case, state information of the object 110 may be determined to be malfunction of the heart, presence or absence of a disease, air pollution, presence or absence of hypoxia, etc. The measured oxygen saturation may be a value that is relative to values of a plurality of reference objects of the same type as the object 110. According to an embodiment of the disclosure, the object 110 may be blood of interest, a first spectrum may be a change of oxygen saturation of the blood of interest over time, and a reference spectrum may be a change of oxygen saturation of a healthy person over time, particularly, in the specific breath interruption time 1230. Then, the processor 230 may determine presence or absence of a disease, air pollution, presence or absence of hypoxia, etc. based on comparison between the first spectrum and the reference spectrum.

According to an embodiment of the disclosure, a change of oxygen saturation may be measured based on a change of portions of spectrum intensities of different two wavelengths. Measuring a change of oxygen saturation based on a change of portions of spectrum intensities of two different wavelengths is well known to those skilled in the art, and therefore, detailed descriptions thereof will be omitted in the present specification. According to an embodiment of the disclosure, a graph 1210 may show a change of oxygen saturation over time, and individual curves may be changes of oxygen saturation of the object 110 over time, measured on different skins. The processor 230 may measure a change of oxygen saturation to determine the breath interruption time 1230, and determine state information of the object 110 based on the change of oxygen saturation in the breath interruption time 1230. A graph 1220 shows another example of changes of oxygen saturation measured on different skins.

Figure 13:
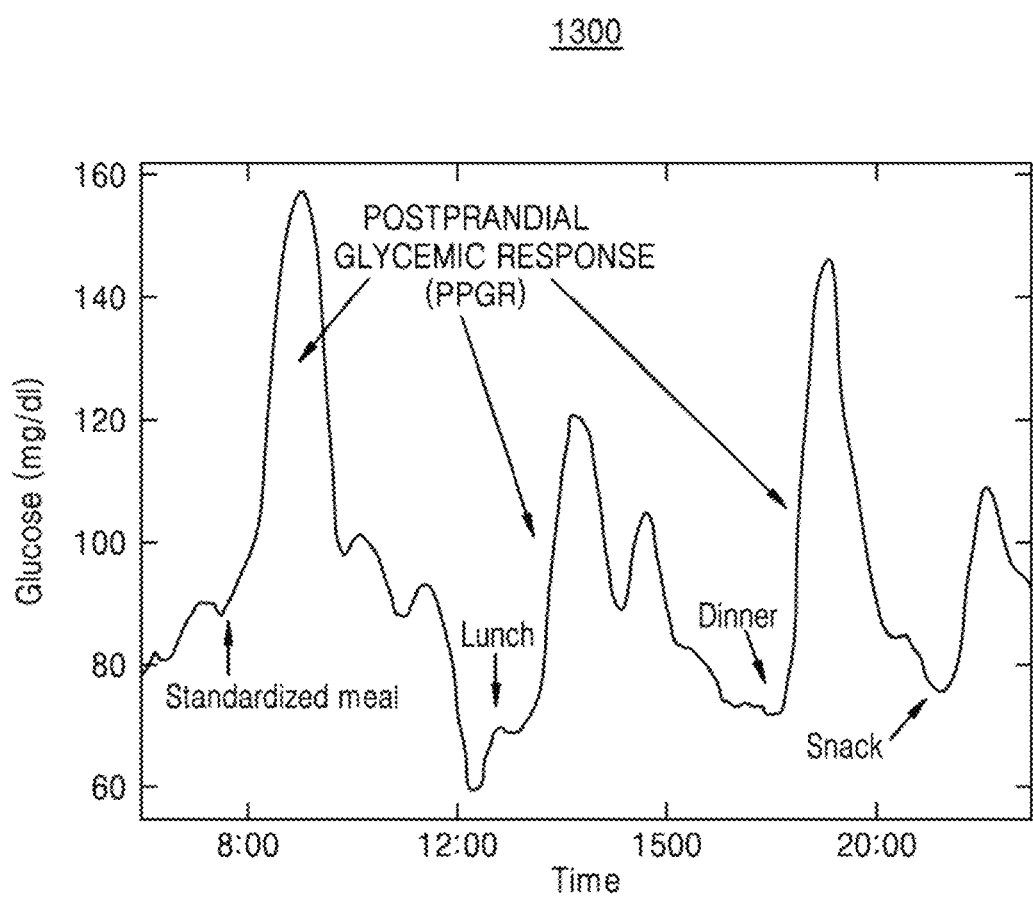
FIG. 13 shows an example of determining state information about an object in an electronic device according to an embodiment of the disclosure.

FIG. 13 shows an example of determining state information of an object in an electronic device according to an embodiment of the disclosure. In this case, the object 110 may be blood, and the electronic device 120 may be a wearable smart watch. A change of blood sugar may be measured based on changes of portions of spectrum intensities of two different wavelengths.

A graph 1300 shows changes of a blood sugar level over time. According to an embodiment of the disclosure, the processor 230 may measure a postprandial glycemic response level, and determine state information of the object 110 based on changes of the postprandial glycemic response level. According to an embodiment of the disclosure, the state information of the object 110 may be whether there is a digestive function problem, whether dietary control is needed, or whether food ingestion is needed, etc.

Figure 14:
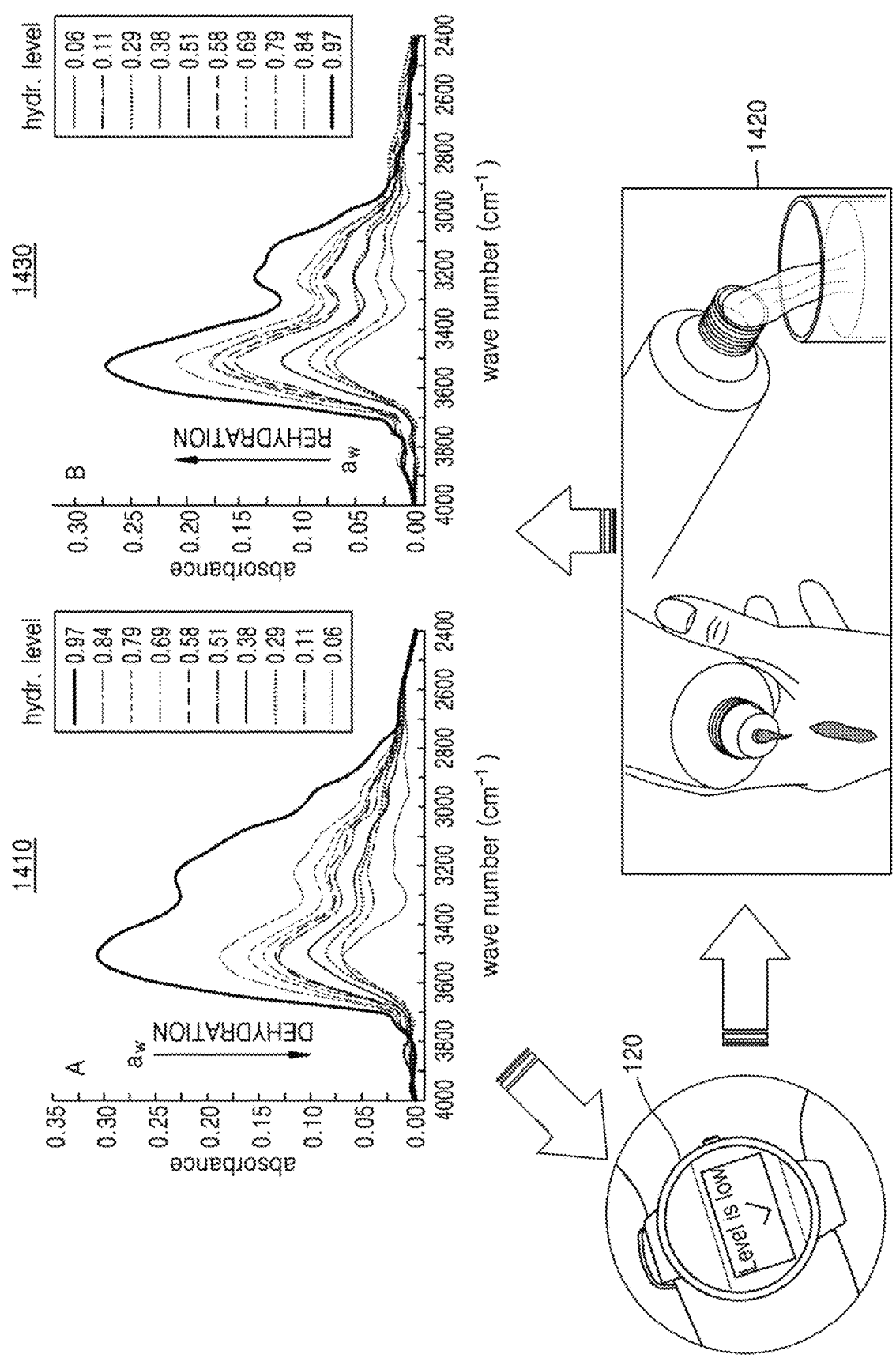
FIG. 14 shows an example of determining state information about an object in an electronic device according to an embodiment of the disclosure.

FIG. 14 shows an example of determining state information of an object in an electronic device according to an embodiment of the disclosure. According to an embodiment of the disclosure, state information of a skin may be determined by using the electronic device 120. In this case, the object 110 may be a skin, and state information of the object 110 may be the age of the skin, skin care effectiveness, etc. A graph 1410 shows absorbance spectrums of individual hydration levels according to wavelengths. Each curve of the graph 1410 represents a hydration level of a skin.

According to an embodiment of the disclosure, as shown in the graph 1410, a hydration level may be reduced over time, and the processor 230 may display information indicating that the hydration level is low through the screen of the electronic device 120, when the hydration level falls below a predefined level. For example, the information indicating that the hydration level is low may be a word "eat water" (not shown). Thereafter, a user of the electronic device 120 may perform a predefined operation (for example, an operation of drinking water or an operation of applying cream) to increase the hydration level, as shown in a graph 1420*a*. According to an embodiment, the electronic device 120 may output a guide for a recommended behavior for the user based on state information. For example, when a hydration level is low, the electronic device 120 may display guide information representing an operation of applying cream, an operation of applying water, etc. through a display, or may output a guide voice through a speaker.

Then, when the user takes an operation of raising the hydration level, the hydration level may increase over time, as shown in a graph 1430. According to an embodiment of the disclosure, the processor 230 may measure a spectrum change of a hydration level of a skin upon dehydration and a spectrum change of a hydration level after rehydration to determine state information of the object 110. For example, the processor 230 may measure a spectrum change from a hydration level 0.97 to a hydration level 0.06 upon dehydration and a spectrum change from the hydration level 0.06 to the hydration level 0.97 upon rehydration, and determine state information of the object 110 based on a spectrum change rate. In this case, the hydration levels to be compared are not limited to 2, and may be set variously by a product designer of the electronic device 120.

Figure 15:
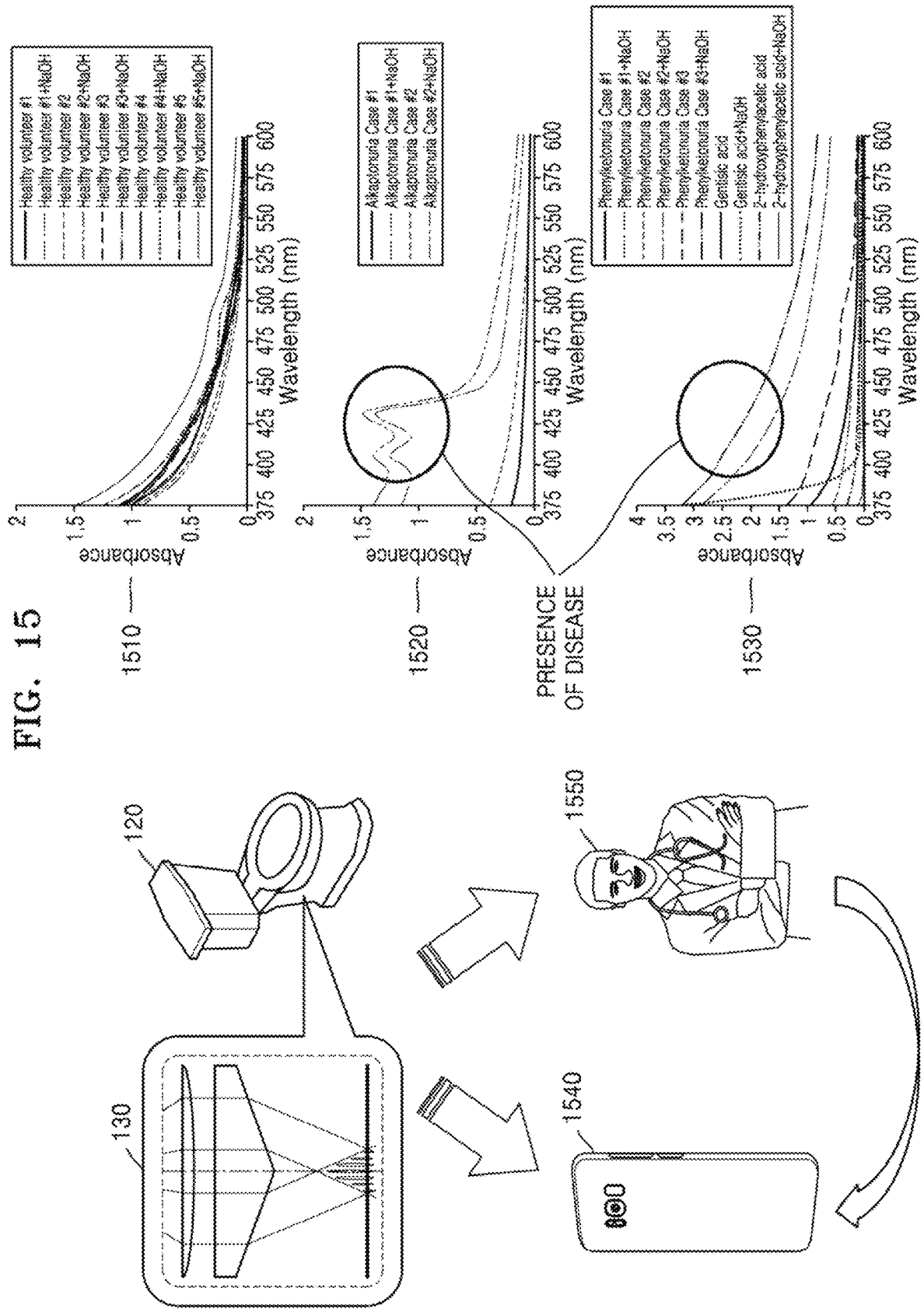
FIG. 15 shows an example of determining state information about an object in an electronic device according to an embodiment of the disclosure.

FIG. 15 shows an example of determining state information of an object in an electronic device according to an embodiment of the disclosure.

According to an embodiment of the disclosure, the electronic device 120 may be a toilet including the optical device 130, and the object 110 may include urine (hereinafter, referred to as a first object) and a mixture (hereinafter, referred to as a second object) of a urine and a compound. In this case, the processor 230 may compare an absorbance spectrum of the first object according to wavelengths to an absorbance spectrum of the second object according to wavelengths to determine presence and absence of a disease, for example, Alkaptonuria or Phenylketonuria.

According to an embodiment of the disclosure, a graph 1510 represents absorbance spectrums of first objects and second objects of healthy persons according to wavelengths. A graph 1520 represent absorbance spectrums of first objects and second objects of persons suspected to have Alkaptonuria according to wavelengths, and a graph 1530 represent absorbance spectrums of first objects and second objects of persons suspected to have Phenylketonuria according to wavelengths. As shown in the graph 1510, the absorbance spectrums of the first objects and the second objects of the healthy persons according to wavelengths start from similar absorption amounts and decrease constantly as the wavelength increases. However, as shown in the graph 1520, the absorbance spectrums of the first objects of the persons having Alkaptonuria according to wavelengths start from low absorption amounts and decrease as the wavelength increases, whereas the absorbance spectrums of the second objects of the persons according to wavelengths start from significantly higher absorption amounts than those of the first objects according to wavelengths and decrease inconstantly as the wavelength increases. As such, the electronic device 120 may acquire information about a disease from an absorbance spectrum of an object, based on characteristics of absorbance spectrums according to diseases.

According to another embodiment, as shown in the graph 1530, absorbance spectrums of a first object and a second object of a person having no Phenylketonuria according to wavelengths start from similar absorption amounts and decrease constantly as the wavelength increases, whereas a absorbance spectrum of a second object of a person having Phenylketonuria according to wavelengths starts from a significantly higher absorption amount than that of a first object and decreases constantly as the wavelength increases, unlike an absorbance spectrum of the first object.

The processor 230 may measure differences of changes of the absorbance spectrums of the first object and the second object according to wavelengths to detect a specific person having Alkaptonuria or Phenylketonuria.

According to an embodiment of the disclosure, the electronic device 120 may transmit information about presence or absence of a disease to an external device 1540 that a user uses. According to another embodiment of the disclosure, the electronic device 120 may acquire only the absorbance spectrums of the first object and the second object according to wavelengths by using the optical device 130, and transmit information about the acquired absorbance spectrums to a doctor 1550. The doctor 1550 may diagnose presence or absence of a disease, and transmit a result of the diagnosis to the external device 1540. For example, the result of the diagnosis by the doctor 1550 may be transmitted to the electronic device 120 through a terminal of the doctor 1550, a medical information server, etc. A subject that diagnoses presence and absence of a disease may be the doctor 1550 or a separate server, although not limited thereto.

Figure 16:
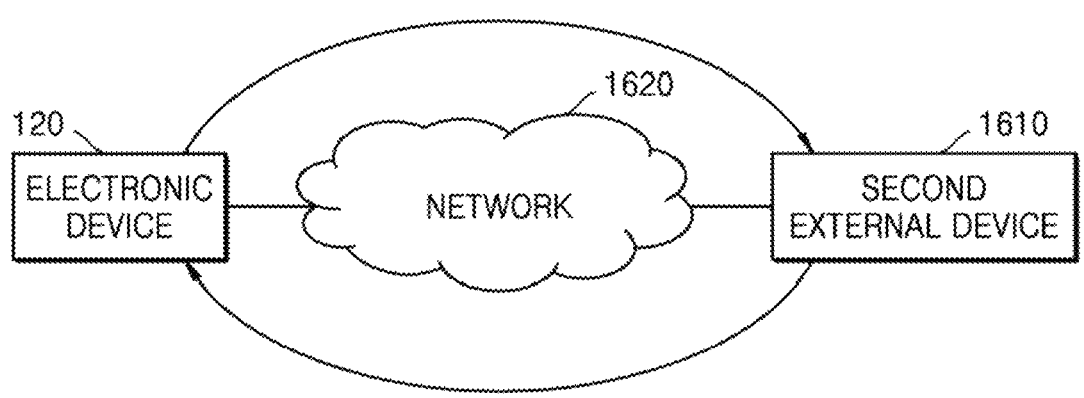
FIG. 16 is a block diagram showing an electronic device and an external device interacting with the electronic device through a network according to an embodiment of the disclosure.

FIG. 16 is a block diagram showing an electronic device and an external device interacting with the electronic device through a network according to an embodiment of the disclosure.

According to an embodiment of the disclosure, to determine state information of the object 110, the processor 230 of the electronic device 120 may access a memory (not shown) of the electronic device 120, or request, when the memory stores no reference spectrum, a second external device 1610 to send a reference spectrum through a communicator (not shown) of the electronic device 120 on a network 1620. The second external device 1610 received a request for the reference spectrum may transmit the reference spectrum to the electronic device 120 through the communicator on the network 1620.

According to another embodiment, the second external device 1610 may include a third electronic device (not shown) to directly perform the method according to the disclosed embodiments. In this case, the electronic device 120 may acquire only the first spectrum of the object 110 and transmit the first spectrum to a server through the communicator, and the second external device 1610 (for example, a cloud server, an artificial intelligent server, etc.) may use the third electronic device of the second external device 1610 to execute a computer program product stored in the second external device 1610 to directly perform the method according to the disclosed embodiments. In this case, the second external device 1610 may transmit a result from the method according to the disclosed embodiments to the electronic device 120, and the electronic device 120 may display the result on the screen.

The communicator may communicate with various types of external devices according to various kinds of communication methods. The communicator may include at least one of a Wireless-Fidelity (WiFi) chip, a Bluetooth chip, a wireless communication chip, and a Near Field Communication (NFC) chip.

The WiFi chip and Bluetooth chip may perform communication according to a WiFi method and a Bluetooth method, respectively. When the communicator uses the WiFi chip or Bluetooth chip, the communicator may first transmit and receive various kinds of connection information, such as a Service Set Identifier (SSID), a session key, etc., to establish communication by using the various kinds of connection information, and then transmit and receive various kinds of information. The wireless communication chip may be a chip that performs communication according to various communication standards, such as the Institute of Electrical and Electronics Engineers (IEEE), Zigbee, $3^{rd}$ Generation (3D), 3rd Generation Partnership Project (3GPP), Long Term Evolution (LTE), etc. The NFC chip may be a chip that operates according to a NFC method using a 13.56 MHz band of various RF-ID frequency bands, such as 135 kHz, 13.56 MHz, 433 MHz, 860 MHz to 960 MHz, 2.45 GHz, etc.

So far, the disclosed embodiments have been described with reference to the accompanying drawings. It will be apparent that those of ordinary skill in the art may make various modifications of the disclosed embodiments thereto without changing the technical spirit and essential features of the present disclosure. Thus, it should be understood that the disclosed embodiments described above are merely for illustrative purposes and not for limitation purposes in all aspects.

The invention claimed is:

1. An electronic device comprising:
an optical element that is fixed and is configured to split incident light thereon reflected from an object into two or more incident light beams traveling along two or more light paths;
an optical sensor that is spaced a separation distance from the optical element such that the split incident light beams form an interference area on a light receiving surface and is configured to detect the split incident light beams; and
at least one processor configured to determine state information about the object based on similarity between a first spectrum acquired from the detected split incident light beams and at least one reference spectrum,
wherein the electronic device changes a wavelength range of a light source that irradiates light to the object according to at least one or a combination of a kind of the object and a kind of state information acquired from the object.

2. The electronic device of claim 1, further comprising a collimator that is fixed and is configured to collimate the incident light reflected from the object.

3. The electronic device of claim 1, wherein the optical element comprises an axicon having two or more faces respectively corresponding to the two or more light paths.

4. The electronic device of claim 1, wherein the optical element comprises a plurality of prisms respectively corresponding to the two or more light paths.

5. The electronic device of claim 1, wherein the optical sensor comprises a plurality of sub sensors having different wavelength ranges, the plurality of sub sensors comprising at least one or a combination of a first sensor having a wavelength range of 300 nm to 500 nm, a second sensor having a wavelength range of 400 nm to 750 nm, or a third sensor having a wavelength range of 750 nm to 1000 nm.

6. The electronic device of claim 1, wherein the at least one processor is configured to perform Fourier transform on the split incident light beams that are converted to electrical signals to obtain amplitude information and phase information, and determine the similarity between the first spectrum and the at least one reference spectrum based on the amplitude information and the phase information.

7. The electronic device of claim 6, wherein the amplitude information and the phase information acquired by performing the Fourier transform respectively correspond to a real part and an imaginary part.

8. The electronic device of claim 1, wherein the at least one processor is configured to acquire type information about the object corresponding to the first spectrum, and compare the first spectrum with the at least one reference spectrum corresponding to the type information to determine the state information.

9. The electronic device of claim 1, wherein the at least one processor is configured to determine state information related to health based on a change of portions of spectrum intensities of different two wavelengths.

10. The electronic device of claim 1, wherein at least one the processor is configured to determine state information related to skin based on a spectrum change of a hydration level upon dehydration and a spectrum change of a hydration level upon rehydration.

11. The electronic device of claim 1, wherein at least one the object comprises a first object corresponding to urine and a second object comprising a mixture of urine and a first compound, and
the processor is configured to determine information related to a disease based on a spectrum of the first object and a spectrum of the second object.

12. The electronic device of claim 1, wherein the state information includes at least one of whether a product is a genuine product or a fake product, freshness of food, ripeness, or a degree of cooking.

13. A control method of an electronic device including an optical element and an optical sensor, the control method comprising:
splitting incident light reflected from an object into two or more incident light beams traveling along two or more light paths in the optical element;
detecting the split incident light beams that form an interference area on a light receiving surface of the optical sensor that is spaced a separation distance; and
determining state information about the object based on similarity between a first spectrum obtained from the detected split incident light beams and at least one reference spectrum wherein electronic device changes a wavelength range of a light source that irradiates light to the object according to at least one or a combination of a kind of the object and a kind of state information acquired from the object.

14. A computer program product comprising a recording medium storing program commands, which, when executed by a processor, cause the processor to perform a method of determining state information about an object, the method of determining the state information about the object comprising:
splitting incident light reflected from an object by an optical element into two or more incident light beams traveling along two or more light paths in the optical element;
detecting the split incident light beams that form an interference area on a light receiving surface of an optical sensor that is spaced a separation distance from the optical element; and
determining state information about the object based on similarity between a first spectrum acquired from the detected split incident light beams and at least one reference spectrum,
wherein an electronic device comprising the processor changes a wavelength range of a light source that irradiates light to the object according to at least one or a combination of a kind of the object and a kind of state information acquired from the object.

* * * * *